US009672324B1

(12) United States Patent
Kasak et al.

(10) Patent No.: US 9,672,324 B1
(45) Date of Patent: Jun. 6, 2017

(54) PEPTIDE PROFILING AND MONITORING HUMORAL IMMUNITY

(71) Applicant: Protobios, LLC, Tallinn (EE)

(72) Inventors: Lagle Kasak, Tallinn (EE); Anri Kivil, Tallinn (EE); Ave Kris Lend, Tallinn (EE); Toomas Neuman, Tallinn (EE); Kaia Palm, Tallinn (EE); Arno Pihlak, Tallinn (EE); Anti Alman, Tartu (EE); Mari-Liis Kruup, Tartu (EE); Meelis Kull, Bristol (GB); Balaji Rajashekar, Tartu (EE); Sulev Reisberg, Tartu (EE); Martin Sauk, Tartu (EE); Gerli Viikmaa, Tartu (EE); Jaak Vilo, Tartu (EE); Anastassia Kolde, Tartu (EE)

(73) Assignee: PROTOBIOS, LLC, Tallinn (EE)

( * ) Notice: Subject to any disclaimer, the term of this patent is extended or adjusted under 35 U.S.C. 154(b) by 210 days.

(21) Appl. No.: 14/079,626

(22) Filed: Nov. 13, 2013

Related U.S. Application Data

(60) Provisional application No. 61/725,963, filed on Nov. 13, 2012.

(51) Int. Cl.
*G06F 19/18* (2011.01)
*C12N 15/10* (2006.01)

(52) U.S. Cl.
CPC ......... *G06F 19/18* (2013.01); *C12N 15/1072* (2013.01)

(58) Field of Classification Search
None
See application file for complete search history.

(56) References Cited

PUBLICATIONS

Bas et al. Rheumatology 2002;41:809-814 (at http://rheumatology.oxfordjournals.org/content/41/7/809.full.pdf).*

* cited by examiner

*Primary Examiner* — Joseph Woitach
(74) *Attorney, Agent, or Firm* — Wagenknecht IP Law Group PC

(57) ABSTRACT

A method of forming a metadatabase of minimal epitope profiles including: performing antibody activity profiling from an immunoglobulin fraction of a plurality of samples to form a data set of peptide profiles for each sample, comparing peptide profiles across different samples, assigning a diagnosis or disorder to differentially expressed meta-profiles, constructing a meta-database containing minimal epitope clusters, constructing a database of peptide frequencies, aligning peptides to define the sequence of minimal epitope, verifying the minimal epitope by harboring a connected identifier, providing an enriched affinity sample, and providing a source data for metadatabase a database underlying it.

19 Claims, 26 Drawing Sheets

AATGATACGGCGACCACCGAGATCTACACTGATCTAGTGGTACCTTTCTATTCTCACTC
TNNKNNKNNKNNKNNKNNKNNKNNKNNKNNKNNKNNKGGTGGAGGTTCGGCCG
AAACTGTTGAAAGTTGTTTAGCAAAATCCCATACAGAAAATTCATTTACTAACGTCTG
GAAAGACGACAAAACTTTAGATCGTTACGCTAACTATGAGGGNNNNNNATCTCGTAT
GCCGTCTTCTGCTTG

FIG. 1A

AATGATACGGCGACCACCGAGATCTACACTGATCTAGTGGTACCTTTCTATTCTCACTC
TNNKNNKNNKNNKNNKNNKNNKNNKNNKNNKNNKNNKGGTGGAGGTTCGGCCG
AAACTGTTGAAAGTTGTTTAGCAAAATCCCATACAGAAAATTCATTTACTAACGTCTG
GAAAGACGACAAAACTTTAGATCGTTACGCTAACTATGAGGGNNNNNNATCTCGTAT
GCCGTCTTCTGCTTG

FIG. 1B

AATGATACGGCGACCACCGAGATCTACACTGATCTAGTGGTACCTTTCTATTCTCACTC
TNNKNNKNNKNNKNNKNNKNNKNNKNNKNNKNNKNNKGGTGGAGGTTCGGCC
GAAACTGTTGAAAGTTGTTTAGCAAAATCCCATACAGAAAATTCATTTACTAACGTCT
GGAAAGACGACAAAACTTTAGATCGTTACGCTAACTATGAGGGNNNNNNATCTCGT
ATGCCGTCTTCTGCTTG

FIG. 1C

AATGATACGGCGACCACCGAGATCTACACTGATCTAGTGGTACCTTTCTATTCTCACTC
TNNKNNKNNKNNKNNKNNKNNKNNKNNKNNKNNKNNKGGTGGAGGTTCGGCCG
AAACTGTTGAAAGTTGTTTAGCAAAATCCCATACAGAAAATTCATTTACTAACGTCTG
GAAAGACGACAAAACTTTAGATCGTTACGCTAACTATGAGGGNNNNNNATCTCGTAT
GCCGTCTTCTGCTTG

FIG. 1D

AATGATACGGCGACCACCGAGATCTACACTGATCTAGTGGTACCGTTTTACTCCCACTC
TGCCGAAACTGTTGAAAGTTGTTTAGCAAAATCCCATACAGAAAATTCATTTACTAACG
TCTGGAAAGACGACAAAACTTTAGATCGTTACGCTAACTATGAGGGNNNNNNATCTC
GTATGCCGTCTTCTGCTTG

FIG. 2A

AATGATACGGCGACCACCGAGATCTACACTGATCTAGTGGTACCGTTTTACTCCCACTC
TGCCGAAACTGTTGAAAGTTGTTTAGCAAAATCCCATACAGAAAATTCATTTACTAACG
TCTGGAAAGACGACAAAACTTTAGATCGTTACGCTAACTATGAGGGNNNNNNATCTC
GTATGCCGTCTTCTGCTTG

FIG. 2B

AATGATACGGCGACCACCGAGATCTACACTGATCTAGTGGTACCGTTTTACTCCCACTC
TGCCGAAACTGTTGAAAGTTGTTTAGCAAAATCCCATACAGAAAATTCATTTACTAACG
TCTGGAAAGACGACAAAACTTTAGATCGTTACGCTAACTATGAGGGNNNNNNATCTC
GTATGCCGTCTTCTGCTTG

FIG. 2C

| Input/motif | E-value |
|---|---|
| 200/193 | 1.3e-372 |

| Input/motif | E-value |
|---|---|
| 2000/1992 | 2.3e-2811 |

| Input/motif | E-value |
| --- | --- |
| 200/88 | 2.5e-180 |

| | Positives | Negatives | |
|---|---|---|---|
| Cases | 42 | 2 | sensitivity: 95% |
| Controls | 1 | 45 | specificity: 98% |
| | | | p-value: 4.581063e-22 |

| | Positives | Negatives | |
|---|---|---|---|
| Cases | 18 | 3 | sensitivity: 86 % |
| Controls | 0 | 23 | specificity: 100 % |
| | | | p-value: 1.291851e-09 |

| | Positives | Negatives | |
|---|---|---|---|
| Cases | 14 | 52 | sensitivity: 21 % |
| Controls | 0 | 66 | specificity: 100 % |
| | | | p−value: 2.827177e−05 |

| | Positives | Negatives | |
|---|---|---|---|
| Cases | 10 | 6 | sensitivity: 62 % |
| Controls | 0 | 16 | specificity: 100 % |
| | | | p-value: 0.0001241315 |

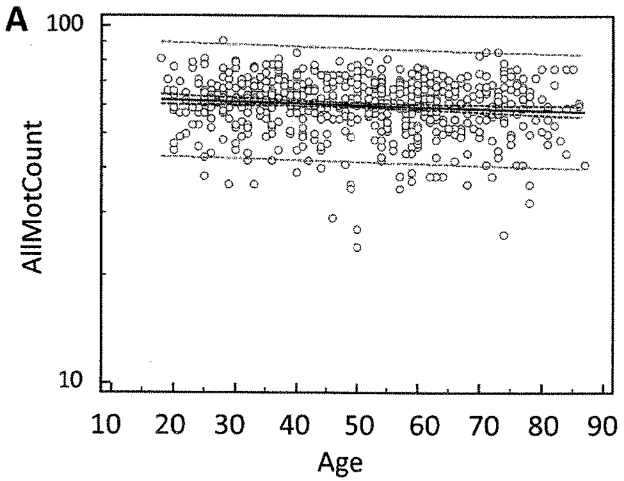

| | |
|---|---|
| Dependent Y | AllMotCount |
| Independent X | Age |

| | |
|---|---|
| Sample Size | 610 |
| Coefficient of determination $R^2$ | 0,01010 |
| Residual standard deviation | 10,3807 |

Regression Equation y = 64,2442 + -0,06242 x

| Parameter | Coefficient | Std. Error | 95% CI | t | P |
|---|---|---|---|---|---|
| Intercept | 64,2442 | 1,3342 | 61,6240 to 66,8643 | 48,1527 | <0,0001 |
| Slope | -0,06242 | 0,02506 | -0,1116 to -0,01320 | -2,4908 | 0,0130 |

Analysis of Variance

| Source | DF | Sum of Squares | Mean Square |
|---|---|---|---|
| Regression | 1 | 668,5594 | 668,5594 |
| Residual | 608 | 65517,4815 | 107,7590 |

| | |
|---|---|
| F-ratio | 6,2042 |
| Significance level | P=0,0130 |

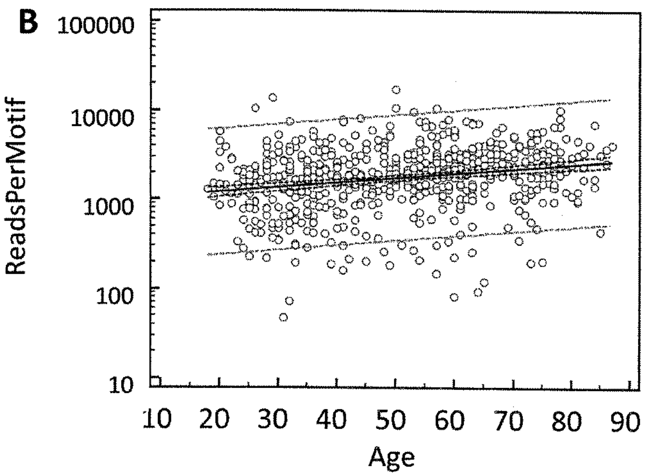

| | |
|---|---|
| Dependent Y | ReadsPerMotif |
| Independent X | Age |

| | |
|---|---|
| Sample Size | 610 |
| Coefficient of determination $R^2$ | 0,03909 |
| Residual standard deviation | 1864,2181 |

Regression Equation y = 1255,1806 + 22,3819 x

| Parameter | Coefficient | Std. Error | 95% CI | t | P |
|---|---|---|---|---|---|
| Intercept | 1255,1806 | 239,5980 | 61,6240 to 66,8643 | 5,2387 | <0,0001 |
| Slope | 22,3819 | 4,5002 | -0,1116 to -0,01320 | 4,9736 | <0,0001 |

Analysis of Variance

| Source | DF | Sum of Squares | Mean Square |
|---|---|---|---|
| Regression | 1 | 85966681,6 | 85966681,6 |
| Residual | 608 | 2112987926,2 | 3475309,1 |

| | |
|---|---|
| F-ratio | 24,7 |
| Significance level | P<0,0001 |

FIG. 23

PEPTIDE PROFILING AND MONITORING HUMORAL IMMUNITY

CROSS REFERENCE TO RELATED APPLICATIONS

This application claims benefit of priority to U.S. Provisional Pat. App. Ser. No. 61/725,963 filed Nov. 13, 2012, the content of which is herein incorporated by reference in its entirety.

TECHNICAL FIELD

The invention relates to the generation of the metadatabase consisting of data constructed based on individual immunoprofiles, more specifically the construction of the minimal epitope defining sequences patterns indicative of epitope specificity and functional activity of immunoglobulins.

BACKGROUND OF THE INVENTION

The immune system protects an organism against diseases by identifying and eliminating the pathogen as well as suppressing the emergence of chronic diseases, such as tumors. In addition, the immune system participates in processes that maintain stable conditions (homeostasis) during development and growth, and following inflammatory reaction or tissue damage. Immune system is classically divided into the innate and the adaptive systems. Adaptive immune system of vertebrate species including human is supplied with an ability to memorize the fingerprints of hostile events threatening organism's physical integrity. The complex immune memory is built upon specialized cells and molecules seeking and destroying disease fingerprints that can be defined as antigens characteristic to either pathogens or structures interpreted as pathogenic (Paul 1993). During the antibody recognition, the immune cells produce antibodies serving as effector molecules against antigens.

Immunoglobulins (Ig) i.e. antibodies are defined as sensory molecules able to detect foreign insult or hostile invaders i.e pathogens and tag them for elimination, and in that way protecting organism against the disease. Next to hostile invaders, such as microbes (virus or bacteria) or parasites threatening the integrity of the host organism, a vaccine that mimics microbial invasion, a host's own naturally occurring molecular entity that has served up it's natural function, or an allergen are considered as immune insults (Berzofsky et al 1993). Also, under special circumstances, the normal constituents of the body can be targeted by the immune system hence can be considered a hostile structures (Suber et al 2008). The fractions of Ig represented in mammals constitute of IgG, IgM, IgE, IgA, and IgD, synthesized by B-lymphocytes in response to antigenic stimuli.

Immunoglobulins are composed of two light and heavy chains that form a Y-like structure that binds antigens with the end of their arms, a structure called paratope. Relevant to the current invention, the antigens recognized by a paratope can be determined by reverse engineering. Molecular libraries that mimic the structure of antigen epitopes including proteins, oligosaccharides, lipopolysaccharides (LPS), glycosphingolipids (gangliosides), and other types of organic and inorganic molecules can be used to characterize naturally occurring epitopes targeted by Igs (Berzofsky 1993). For characterization, various technologies including ELISA, RIA, and interaction display methods such as phage display can be used. Peptide substitution analysis and random display mapping experiments have shown that core B-cell epitopes are relatively short ranging between 3-12 amino acids, borders of the mapped epitope are sharp and only some residues are critically required for interaction (Buus et al 2012). Different antibody epitope mapping methods have reported, yet as a rule, the single amino acid resolution epitope profiles for most of the monoclonal and polyclonal antibodies are not commonly available. There is a need for simple, robust, high-throughput, accurate and cost-effective epitope mapping method, enabling to map linear and conformational epitopes of mono- and polyclonal antibodies.

Igs play an important role in both health and disease, and, thus, their occurrence in the body reveals relevant clues about the health condition. The invention is based on the following statements: (1) Ig composition undergoes disease-specific changes, (2) the changes and shifts are preserved in the immune memory, and (3) the recorded events, if interpreted in the right way, can be used to make decisions about the health of the ogranism.

It has been demonstrated, that antibodies as well as antigens are useful in clinical immunodiagnostics, differential diagnostics, determination of prognosis, and informed decision-making about treatment options. To this end there also remains a need to develop methods to further characterize the immune system.

Traditional clinical immunodiagnostics is based on blood tests that apply circulating Igs as the detectors of antigens, or the precise copies of previously known antigens as detectors of seroreactivity. However obtaining either antibodies with specific affinity or whole antigenic molecules is costly and labor-intensive.

The invention describes a method that by generating a metadatabase enables to detect any immune memory-related health condition of an organism by catalogizing information related to the organism, related but not limited to the patterns of macromolecules that are structurally similar to naturally occurring disease antigens. With the method huge amounts of data of Ig minimal epitopes reflecting antigenic regions of the known and yet to be defined, novel substances are defined and simultaneously provided compiling a metadatabase. As the presence and levels of these minimal epitope-defining sequences can be measured all at once in a massively paralleled manner, eg numerous samples simultaneously (in DESCRIPTION OF INVENTION), the qualitative and quantitative variation of the minimal epitope defining sequences identified by the method, generate characteristic to an individual sample profiles that ultimately contribute to defining the antibody-activity related antigenic signatures reflecting the health medical conditions. If a statistically significant match with a disease or disorder is found, a diagnosis or other medical decision can be proposed. The invention is termed as Mimotope Variance Analysis (MVA).

SUMMARY OF THE INVENTION

The present invention addresses the needs described and provides related benefits. This is accomplished through methods described herein, which include a method of generating a metadatabase, the method including: providing a characteristics of the minimal epitope defining sequences, wherein the sequences are obtained from the clustering of peptides by sequence and frequency of occurrence as immune system targeted antigens in a sample across many hundreds of samples. This database enables to filter individual patterns as well as immunocharacterize a group of population based on some predefined parameter (i.g. disease, age, gender).

Providing a tool for data generation and verification comprising of identificator-proteinaceous antigen compound.

Providing an affinity selected sample, enriched towards higher purity.

In one aspect, a method of forming a metadatabase of minimal epitope profiles is provided, the method including providing a plurality of biological samples; performing antibody activity profiling of highly parallel, high-throughput selection of peptide-antigens from an immunoglobulin fraction of the samples to form a data set of peptide profiles for each sample, wherein the peptide profiles comprise antigen-antibody interaction sequences, thereby permitting characterization and cataloging of minimal epitope definition patterns; comparing peptide profiles across different samples to generate a meta-profile defined by an amino acid sequence of the motif and its frequency pattern; assigning a diagnosis or disorder to differentially expressed meta-profiles generated from samples affected by the diagnosis or disorder; constructing a meta-database containing minimal epitope clusters (motif_summary), defined according to the peptide frequency patterns over multiple samples; constructing a database of peptide frequencies (pep_summary), where frequency of occurrence of each of the peptide antigen is recorded for all samples; aligning peptides of a characterized sample to reveal similarity in amino acid sequence thereby defining the sequence of the minimal epitope; verifying the minimal epitope by harboring a connected identifier—proteinaceous antigen compound wherein the identifier is a molecule or substance allowing later identification of the respective peptide identity; providing an enriched affinity sample for minimal epitope defining sequence generation; and providing a source data for metadatabase and any database underlying it by any amplification and sequence identification method.

In some embodiments the identificator-protein system is a random phage display peptide library that displays a plurality of random peptides, wherein phage members of the phage display library include an amplicon comprising a DNA region encoding different random peptides flanked by adaptor regions and a unique bar code sequence; providing a sample of immunoglobulins (Ig) or immunoglobulin fragments; pre-clearing the inviolate random phage display library by exposing the phage members to a control and removing bound phage members from the random phage display library, the control sample comprising but not limited to capture reagent immobilized immunoglobulins (Ig), capture reagent immobilized competitive compound, surface materials, such as plastic and/or any other substance for which the undesired response should be removed; pre-absorbing the sample of immunoglobulins (Ig) to a control sample to provide a block against nonspecific binding of phage members, the control sample comprising a mutant phage-host lysate; construction and providing of a mutated phage used as a control sample in immunoglobulin pre-absorption, wherein the mutated phage presents a highly inefficient amplification abilities; providing a capture reagent mounted to a solid support, the capture reagent configured to capture the immunoglobulins (Ig) or immunoglobulin fragments; mixing the pre-cleared random phage display library, the pre-absorbed sample of immunoglobulins (Ig) and mounted capture reagent under conditions that permit specific binding between the random peptides with immunglobulins and capture of the immunoglobulins with the capture reagent; collecting the solid support to collect phage members bound to the immunglobulins; isolating the amplicons from collected phage members under specified conditions; amplifying the isolated amplicons under specified conditions; normalizing the amplified amplicons so that each barcode is about equal; sequencing the DNA region of the normalized amplicons and optionally aligning the sequenced DNA regions to form a consensus sequence; translating the sequenced DNA regions or consensus sequence to form a datasets of peptide-antigens capable of binding to the immunoglobulin or immunoglobulin fragments; and assigning the datasets of peptides to a database.

In some embodiments, the random peptides are twelve amino acids in length and the unique bar code sequence has 4 nucleic acid bases of different order than those in other amplicons, each nucleic acid base selected from the group consisting of guanine (G), adenine (A), thymine (T) and cytosine (C). In other methods the unique bar code sequence has 6 nucleic acid bases of different order than those in other amplicons, each nucleic acid base selected from the group consisting of guanine (G), adenine (A), thymine (T) and cytosine (C). This permits labeling of each phage member and permits the use of selective polymerase chain reaction (PCR) through the use of primers targeting the adaptor regions and the unique bar code.

The invention is shown to be effective using a variety of samples. The sample include a monoclonal antibody fraction thereby establishing a epitope profile for the monoclonal antibody from the library of peptides or a polyclonal antibody fraction. In some embodiments the sample is collected from a population of humans, such as from sera, thereby forming a minimal epitope defining sequence profile group of the population. Further, collection can be from a single individual or a group of individuals grouped according to a group characteristic for generating a peptide or minimal epitope defining sequence profile for comparison to a peptide profile group. In such instances the difference in peptide profile can be assigned to the single individual or the group of individuals as indicative of a particular condition and thus provide diagnostic or possible therapeutic utility. In particular, such a peptide profile may be associated with the individual or group of individuals that are suffering from a medical condition. The method according to claim 1, wherein the sample of immunoglobulins (Ig) or immunoglobulin fragments is obtained from sera or plasma.

The control sample provides a block to prevent unspecific binding between Ig and antigenic peptide library. Accordingly, the control sample can be sera. Among the useful capture reagents, protein A or protein G fixed to a solid support in the form of a magnetic bead is shown effective.

In some embodiments, peptides within the library of peptides are aligned to reveal differences in amino acid sequence of greater or lesser implication on epitope binding thereby assigning more selective or less selective positions within the library of peptides.

In another aspect of the invention, a method of forming a vaccination peptide profile is provided, the method including: performing the method above with samples from a time point before a vaccination and a time point after a vaccination to form a peptide profile for each time point; and comparing the peptide profiles between time points to establish a peptide profile indicative of vaccination.

BRIEF DESCRIPTION OF THE DRAWINGS

FIG. 1A provides a sequence of a 242 bp long MVA amplicon constructed by PCR, designated SEQ ID NO. 1.

FIG. 1B, shows the positioning of sense SEQ ID NO. 2 and antisense SEQ ID NO. 3 adaptor regions complementary to the M13KE phage display vector. FIG. 1C shows the positioning of a six bp barcode (index) sequence and a four bp bar code for sequencing analysis at the 3' end in underline format and a 12-mer random peptide encoding DNA sequence (NNK)12 (SEQ ID NO. 6), where N is either A, G, T or C, and K is either G or T, is shown in bold. FIG. 1D shows the positioning of 5' (SEQ ID NO. 7) and 3' (SEQ ID NO. 8) adaptor sequences.

FIGS. 2A-C depict a 194 bp long MVA library amplicon (SEQ ID NO. 9) derived from M13KE_mWT as template containing bar code mutated 5'-and intact 3' adapter sequences with attached sequences. In FIG. 2A, sequences of the 5' (SEQ ID NO. 10) and 3' (SEQ ID NO. 3) adapters attached by the PCR are underlined. In FIG. 2B, sense (SEQ ID NO. 11) and antisense (SEQ ID NO. 12) adapter 3' regions complementary to the M13KE vector are underlined with mutated basepairs disrupting the binding of the sense adapter with M13KE_mWT vector shown in bold and at increased font size. In FIG. 2C, a six basepair long barcode incorporated into the 3' adapter sequence is underlined. As compared with the MVA library sequence depicted in FIGS. 1A-D, sequences encoding 12-mer random peptide (SEQ ID NO. 27) and GGGS linker (SEQ ID NO. 28) are absent from M13KE_mWT vector.

FIG. 8 presents average Cy3 signal intensity of duplicate samples tested in two dilutions of the primary antibody. Native myc peptide EQKLISEEDL (SEQ ID NO. 20) presenting phage PC87 specifically binds with 9E10 antibody, and reacts also with MVA-identified phages PC109 and PC110, containing the core motif LISE..[L/M] (SEQ ID NO. 22). Only background signal was detected when phages encoding FLAG motif were used as controls of analysis. No signal was detected when MASH1 motif-containing phages, or HEK293 cell lysates, transfected with plasmid encoding human MASH1 protein or mock vector, were analyzed.

FIG. 9 presents average Cy3 signal intensity of duplicate samples tested in two dilutions of the primary antibody. FLAG antibody recognizes specifically native FLAG tag DYKDDDDK (SEQ ID NO. 19) presenting phage PC86 and MVA-identified PC100 peptide that contained FLAG motif with the sequence DYK..D (SEQ ID NO. 4). Higher antibody concentrations led to the improved signal detection when PC104, PC105 and PC107 phages, containing the minimal FLAG motif with the sequence YK.D were analyzed. Background signal was detected when phages encoding myc (PC87, PC109 and PC110) or MASH1 motif (PC38 and PC88) were used as controls for analysis.

FIG. 10 presents the average of Cy3 signal intensities of the duplicate samples tested. Phage PC38 presenting a MVA-identified peptide with the sequence HACATSLCEAAL (SEQ ID NO. 21) shows specific binding with anti-MASH1 monoclonal antibody. Replacement of the conserved threonine (T) with alanine (A) in the MVA-identified MASH1 motif with the sequence C..T.C eliminated specific binding of PC88. Binding was also detected when HEK293 cell lysates transfected with plasmid encoding human MASH1 protein was used for analysis. Background signal was observed when phages encoding myc or FLAG motif were used as controls.

FIG. 23 depicts the age dependence of IgG clonal diversity and clonal abundance. Panel A—a scatter blot showing motif count of 500 most frequent peptides compared to age. Panel B—scatter blot of average read sum per motif compared to age. The regression line with 95% confidence interval (red dashed lines) and 95% prediction interval (orange dashed lines) is shown. The regression analysis statistics are presented below each respective scatter blot.

DETAILED DESCRIPTION

Figure 3:
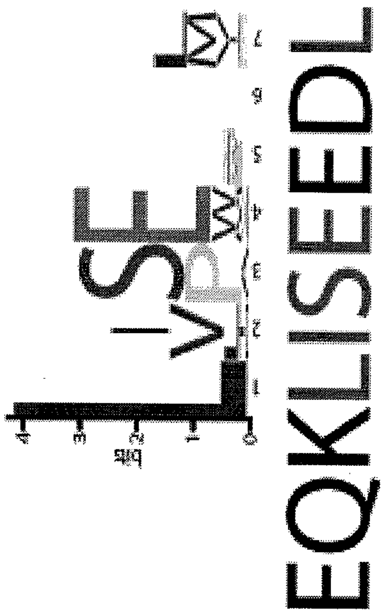
FIG. 3 depicts a printout of the identification of the depth of the anti-c-myc 9E10 epitope by MVA as performed in Example 2. Specifically, 200 peptides that were the most downregulated upon the competition analysis with EQKLISEEDL peptide (SEQ ID NO. 20).

Described herein are methods that can be utilized to analyze and profile the composition of a complex antibody mixture characteristic to different physiological conditions in an intention to identify the target mimotopes identified as minimal epitope defining sequence for diagnostic and therapeutic purposes. This is achieved through the method of meta database, comprising of the data collection for antibody activity profiling with highly parallel, high-throughput selection of peptide-antigens of any immunoglobulin fraction, and sequence identification enabling simultaneous characterization and cataloging of antibody activity profiles and minimal epitope defining sequences, providing construction of peptide clusters database, according to peptide frequency patterns over the large amount of samples. In one aspect of the invention, a method of forming a minimal epitope defining sequence profile is provided, the method including: a method for minimal epitope defining sequence generation and verification; an identificator—protein compound, wherein the identificator is a nucleic acid; a method wherein the nucleic acid sequence and respective protein comprises of a peptide library wherein the library is in the composition of an amplicon comprising of a DNA region encoding different random peptides flanked by adaptor regions and a unique bar code sequence; providing a sample of immunoglobulins (Ig) or immunoglobulin fragments; pre-clearing the protein compound containing peptide library; pre-absorbing the sample of immunoglobulins (Ig); a capture reagent mounted to a solid support; mixing the pre-cleared protein compound containing peptide library, the pre-absorbed sample of immunoglobulins (Ig) and mounted capture reagent under conditions that permit specific binding between the peptides with immunglobulins and capture of the immunoglobulins with the capture reagent; collecting members of protein compound containing peptide library bound to the immunglobulins; isolating amplicons from collected library members; sequencing the DNA region of the normalized amplicons; compiling the library of peptides to a database; generating minimal epitope sequence profiles and assigning them to metadatabase.

The tool for providing input information for metadatabase can be any system that enables to connect an identification factor, such as but not limited to nucleic acids, with the proteinaceous antigen providing system. Some of these methods include but are not limited to yeast display, bacterial display, cell surface display, in vitro display techniques.

The amplicon is a nucleic acid segment, which is ligated into the phage vector, and includes a DNA region encoding different random peptides flanked by adaptor regions and a unique bar code sequence. DNA encoding the random peptides can be any suitable length; however, DNA segments encoding 12 amino acids were found to be particularly useful. However, it can also be acceptable to use lengths that are shorter, such as between 6-12 amino acids and lengths that are longer, such as 12-18 amino acids. Naturally one skilled in the art would recognize that providing DNA in the phage system permits the use of the degenerate code of DNA. That is, some amino acids may be encoded by more than one codon. The DNA region itself may be synthesized using oligonucleotide synthesis technology.

Adaptor regions may be any suitable nucleic acid sequences and may be designed in combination with amplification primers for improved amplification of the DNA region. In regards to primers, the amplicon includes a unique bar code sequence having at least 4 nucleic acid bases of different order than those in other amplicons, each nucleic acid base selected from the group consisting of guanine (G), adenine (A), thymine (T) and cytosine (C). Four distinct sequences permits approximately 256 different identifiers.

Preferably, this is increased to 6 nucleic acid bases of different order than those in other amplicons, which would results in about 4,096 unique bar codes. This permits labeling of each phage member and permits the use of selective polymerase chain reaction (PCR) through the use of primers targeting the adaptor regions and the unique bar code Samples can either be derived from body fluids (such as whole blood, serum, semen, saliva, tears, urine, fecal material, spinal fluid), from tissue biopsies or from manually prepared complex mixtures of synthetically produced proteins. Suitable samples can be of hominoid (human, ape) or animal origin (e.g. cow, pig, horse, sheep, dog, cat, etc.). In case of comparative studies, one sample is obtained from a diseased individual and a second sample is obtained from a non-diseased (normal/control) individual or group of individuals. To this end, different populations of subjects can be compared, such as those suffering from disease, subjects those having a different disease state, vaccinated versus non-vaccinated and the like.

While subjects or populations of subjects can be the object of the study, the invention can also be used for to map specific proteins, such as for epitope mapping of antibodies, including polyclonal and monoclonal antibodies. For instance, the sample can include a monoclonal antibody fraction thereby establishing an epitope profile for the monoclonal antibody from the library of peptides or a polyclonal antibody fraction.

To prevent unspecific binding or binding between assay components and the immunoglobulin (Ig) or antibody fragments at the time of display the Ig is typically pre-coated or blocked with control sample, which can include lysed phage, mutant phage, phage host, sera, plasma, an Ig solution or the like as consistent with the assay. Similarly, to prevent unspecific binding of the phage, the phage library should be exposed to a control pool of immunoglobulins or immunoglobulin fragments and removed.

Most often the screening/enrichment of the display libraries is carried out using (bio)panning method. Panning is an affinity selection technique which selects for proteins/peptides that bind to a given target. To this end, a capture agent is bound to a solid support for capturing Ig and thus bound phage. Capture agents can bound to a variety of solid supports, among which include, beads (agarose, latex, polystyrene, magnetic), which can be functionalized with tools used for immobilization of the capture agent using approaches consistent with the solid support and the particular capture agent, such as through the use of functional groups like —COOH, —SH and the like; wells of a microtiter plate; or chromatography columns. Alternatively, the capture reagent can include an affinity tag, such as protein/peptide tags like biotin/avidin or glutathione/GST, metal affinity tags like Ni/Co/6xHis and the like. Among the useful capture reagents, protein A or protein G fixed to a solid support in the form of a magnetic bead is preferred.

The sample is incubated with a library of genetic packages displaying the (recombinant) proteinaceous binding domains (e.g. peptides) and with or afterwards with the capture reagent bound to the solid support. Since the binding pairs of peptide and Ig from the sample are captured by captured agent with solid support, their removal is performed consistent with the approach used in the solid support thereby separating bound peptide from unbound genetic packages. The separation and removal of unbound peptides can be enhanced by introducing several washing steps. Once purified, the phage can be lysed and the amplicons collected or directly amplified using suitable primers.

The first step of data analysis is the construction of a peptide frequency database, herein pep_summary cataloging the frequencies of sequenced peptide-antigens within each sample and across all samples.

Then, the peptide frequency is normalized first by the sum of counts of all peptide antigens obtained in the respective sample in order to compensate for the differences of the physical differences of the sample, and second by the sum of counts of internally added control peptide antigens that contains the sample identifier (barcode sequence) in order to compensate for the physical handling of the sample.

User could analyze each sample separately or series of samples at a time in order to define the peptide antigen motifs that are present in unique or common peptides in the user defined sample. This approach is relevant to analyzing dynamic series of samples, such as in case of vaccination or immunizaton, or in competition analysis of defining single poly- and monoclonal antibody epitopes.

However, in case the complexity of a sample profile is high, such as for sera, plasma or other bodily or similar fluids containing antibodies, only the dominant peptide-antigen motifs can be identified by analyzing one sample at time. Therefore, for in-depth serum profiling, a metadatabase containing meta-profiles deduced from original dataset of peptide antigens characteristic to a sample or sets of samples must be constructed.

The meta-database construction is based on the analysis of the peptide frequency patterns across unique serum samples, such that ultimately unique individual profiles from the pep_summary database containing all the data of the peptides identified in individual samples will be filtered and a new database filterMS comprising peptides where observed frequency counts in at least across two samples is >10 is constructed. Therefore, all the peptides specific to an individual sample will be omitted from further analysis. pep_summary and filterMS databases are dynamically changing and when new peptide-antigen results are included, database is rescanned using the same criterions as described above. Peptides that were first omitted from the initial version of filterMS may now satisfy the respective criterions.

Antibodies are in constat change and vary for their presence from individual to individual. Therefore, statistical probability exists that some samples (anchor samples) will contain excessively more antibodies directed against the same epitope than other samples where the same antibodies are present in minuscule amounts. Here the parallels can be drawn with the exemplified monoclonal antibody titration experiments where observed top list of the most frequent peptide-antigens (competitors) in the sample that contains high titer antibody, is the same as the top list of peptide antigens in the sample where the antibody in a highly dilute setting is used. Therefore by defining the complete set of peptide-antigens, constituting a unique binding specificity profile of a specific antibody by utilizing an anchor sample, one could increase the resolution of profiling by defining a small set of peptides acting as a immune reaction predictor i.e. meta-profile.

Increasing the number of samples in the database will constantly increase the depth of the meta-patterning enabling to identify profiles that are rare in population. Similarly, constant improvements of technology, including that of next generation sequencing, enhances the resolution of the method and allows to defines less abundant peptide antigen profiles.

Peptides in the filterMS database are organized based on summarized peptide counts and Pearson correlation coefficient is used for comparing the most frequent peptide (query peptide) counts against the counts of the other peptides present in the filterMS database. In case, the correlation coefficient is above threshold pcc>0.4, the initial cluster is formed containing the range from about 5 to 150 peptides, and then aligned to define the consensus motif Since each position, in for example, a peptide with the length of 12 amino acid could be encoded by the 20 natural amino acids, the total number of possible unique variants resembling the peptide is theoretically $12^{20}$. Antibody paratope generally requires for the interaction with the antigen 3 to 8 more or less fixed amino acids of the antigen and although the epitope position is unfixed in the antigen sequence with the exception of N-terminally locating epitopes, the probability that clear consensus is forming in a small set of peptides by a chance is negligible. In case of a motif defining a minimal binding sequence is not found or it is present in a few (rare) peptides, a new search with the next query peptide will be initialized.

Subsequently, all the peptides in the filterMS database containing the motif identified will be further analyzed by FUZZPRO. Depending of the length of the motif and the level of conservation across samples, loose search parameters are allowed to include all possible peptide combinations that might belong to the respective cluster. Again, filtering the FUZZPRO search results using Pearson correlation coefficient will be conducted and peptides below the threshold level (pcc<0.3) are left out from the final cluster. Finally, peptides assigned to the cluster are removed from the filterMS database and filtered on the basis of summarized counts. Presence of the consensus motif among the 20 most frequent peptides of the cluster will again be verified by motif analysis tools. Meta-profile describing the immune reaction against a particular epitope across all samples is generated as an average of frequencies of occurrence of the 20 most frequently observed peptide antigens composing the respective cluster. Defined meta-profile is added into the dynamic metadatabase named motif-summary. Tools like 2_group_comparison or motif combination could be used in order to find any meta-profiles that are biased towards user defined samples.

EXAMPLES

Exemplary embodiments of the invention are described below with reference to the drawings.

Example 1

Generation of a B-Cell Epitope Profiling Database

In the era of next generation techniques and bioinformatics, a single experiment cannot compete with the systematic analysis that relies on the power of many. Herein, next generation sequencing is utilized for the generation of global profiles of immunoglobulin-binding peptide antigens. Highly parallel, high-throughput unbiased peptide-antigen selection and sequence identification approach, MVA, is flexible and can be applied to any immunoglobulin fraction enabling simultaneous characterization and cataloging of monoclonal, polyclonal and global epitope (immunome) profiles. Constructed database serves as a resource for group, class, family or single organism (individual) specific epitope profile discovery as described in, but not limited to, the subsequent examples.

As a result of the workflow described below, a large peptide database was constructed including information of peptide-antigens from sera, plasma or immunoglobulin samples, including human and non-human (animals) species. The peptide-antigen database allows to further simplify data analysis steps and enables a systematic discovery from a single epitope to a systems biology approach of the global immunome (total humoral response) as described in the subsequent examples.

1-1: Construction of the MVA Library

MVA library was constructed by PCR using a pre-made 12-mer random phage display library (#N0316S, New England Biolabs, MA, USA). FIGS. 1A-D show the MVA amplicon structure (SEQ ID NO. 1) representing the template sequence of the constructed library, which includes a DNA region encoding randomized peptide insert (SEQ ID NO. 6) and unique bar codes enabling multiplexing. The 5' regions of the sense (SEQ ID NO. 2) and antisense primer (SEQ ID NO. 3) include the Illumina adapter sequences and the 3' region is complementary to the M13KE display vector.

The protein pIII encoded by M13KE_mWT is phenotypically identical with that of the wild-type M13 phage, encoded by M13KE vector. However, as shown in FIG. 2, point mutations shown in bold and with increased font in FIGS. 2A-C, introduced into the plasmid M13KE_mW disrupt the 5' PCR adapter primer binding with the M13KE_mWT template, yielding in a highly inefficient PCR amplification.

1-2: Preparation of the Pre-Absorption Solution.

Using any protein-peptide selection display system, such as for example M13KE phage (#N0316S, New England Biolabs, MA, USA), it is necessary to pre-absorb immunoglobulins (Igs) before affinity selection of peptide antigens to avoid unspecific binding of Igs to the recombinant host, plastic or other similar types or targets. For that, a pre-absorption of the sample (either sera, plasma or Ig solution) is carried out. In brief, the bacterial host strain ER2738 is infected with the M13KE_mWT phage and a bacterial lysate is prepared for immunoglobulin pre-absorption. Large scale preparation of pre-absorption solution is carried out at a time, in quantities sufficient for hundreds of parallel peptide-antigen affinity selection experiments.

1. 4 ml of LB media is transferred into the autoclaved glass tube and inoculated with fresh ER2738 colony. The starter culture is incubated overnight (ON) at 37° C. at 180 rpm with shaking in the incubator shaker CERTOMAT® H (Sartorius Group, Gottingen, Germany).
2. The overnight ER2738 culture is diluted 1:100 into the 300 ml of the autoclaved LB media and bacteria are infected with 15 μl M13KE_mWT phage stock. The phage-bacteria suspension is then divided between three 500 ml Erlenmeyer flasks.
3. The flasks are incubated for about 6 hours at the shaking speed of 180 rpm and temperature at 37° C. After that, the cultures are pooled.
4. An aliquote of 700 μl from the pooled suspension is taken for qPCR analysis and ssDNA preparation.
5. The cultured suspension is transferred to 50 ml tubes, 40 ml each.
6. The lysates are sonicated on ice with VCX 130 Vibra-cell™ sonicator (Sonics and Materials INC, USA) using the following settings TIME: 3 min; PULSE ON 10 sec; PULSE OFF 30 sec; AMPLITUDE 50%.
7. The sonicated lysate is pooled and centrifuged for 10 min at 15557 g.
8. After this the cleared supernatant is poured into the new tubes and stored at −20° C.

9. M13KE_mWT ssDNA is purified from 0.5 ml of the supernatant as described (Wilson R. K, 2003) and the correct amplification of M13KE_mWT is verified by Sanger sequencing.
10. Phage supernatant containing the amplified phage is diluted in MQ and the concentration of M13KE_mWT DNA in the pre-absorbtion solution is determined via standard qPCR using M13KE vector specific primers:
    SEQ ID NO. 13 real_M13KE_s 5'-TGTACTTT-GTTTCGCGCTTG-3';
    SEQ ID NO. 14 real_M13KE_as 5'-AACGGCTACA-GAGGCTTTGA-3'.

1-3a: Pretreating Magnetic Beads with Glycine

Protein G or protein A beads that bind IgG or IgA immunoglobulin fractions respectively with high affinity, are used alone or in combination for profiling this component of immune response. Alternatively, for profiling the total immunoglobulin spectra including IgM, IgA, IgE and IgD fractions, single chain variable fragments (ScFv) and Fab fragments or immobilized protein L beads can be used in combination.

Pretreatment of protein G and protein A Sepharose (magnetic) beads with high pH glycine reduces nonspecific Ig binding to the beads (Williams A. J. K, 2006). Herein, protein G magnetic beads sufficient for 100 affinity selection analysis are initially subjected to pretreatment as described below. Subsequently, the pretreated protein G magnetic beads are mixed with the precleared NEB phage library prepared as described in the part "Preclearing of the random peptide phage library". This mixture will be subsequently mixed with pre-absorbed Igs prepared in section "Pre-absorption of the sera, plasma or immunoglobulin samples" and immunoreactive peptide antigens will be affinity selected from the random peptide library as described in the part "Affinity selection of the phage-displayed immunoreactive peptide antigens".

1) The protein G magnetic beads are spinned for 1 min at 1000 g and magnetically captured.
2) Beads are washed twice with 1 ml of PBS-0,1% Triton-X-100 (PBS-TX).
3) This is followed by washing once with 1 ml of 0.2M glycine (pH 10.6).
4) Then, the beads are resuspended in 1 ml 0.2M glycine (pH 10.6) and incubated while rotating ON at 4° C.
5) The next day, the supernatant is removed and the beads are washed three times with 1 ml of PBS-0,1% Tween20 (PBS-T0,1%).
6) After washes, the beads are resuspended in 1 ml of PBS-T0,1% and all five tubes of beads were pooled together into the 50 ml tube containing 25 ml of precleared random peptide phage library.

1-3b: Preclearing of the Random Peptide Phage Library

The preclearing protocol of the random phage library (NEB or like) for affinity selection of 100 Ig samples is described as follows. The protein G magnetic bead slurry capable of binding>400 μg human IgG are mixed with human IgG (pool of >1000 individuals) in order to eliminate phages that nonspecifically bind to either immunoglobulins or beads.

1) The protein G magnetic beads from 1 ml of the beads slurry (#S1430, NEB) are captured with 6-tube Magnetic separation rack (S1506S, NEB).
2) The beads are washed twice with 1 ml of PBS-TX and once with 1 ml of PBS-T0.1%, subsequently resuspended in 1 ml of PBS-T0.1% and transferred into 50 ml tube.
3) This is followed by the addition of 500 μl of Ph.D.™ Phage Display Peptide library (#E8111L, NEB), 5 ml of pre-absorption solution containing sonicated M13KE_mWT lysate and 50 μg of the pooled control sera (I4506, Sigma Aldrich) to the resuspended beads.
4) The reaction volume is brought to 25 ml with PBS-T0.1% and the sample is incubated by rotating overnight at 4° C.
5) The next day, the samples are centrifuged for 2 min at 1000 g, the beads are captured and the supernatant is transferred into a fresh tube.
6) The supernatant that contains the precleared phage library is centrifuged for 10 min at 15557 g using a fixed angle rotor and then transferred to a fresh tube.

1-4: Pre-Absorption of the Sera, Plasma or Immunoglobulin Samples

For substracting the antibody reactivity that specifically targets bacterial or phage capsid proteins, sera, plasma or the immunoglobulin samples are preincubated with the sonicated phage-bacterial lysate. Subsequently, the pre-absorbed immunoglobulins are mixed with the random peptide phage library followed by the affinity selection procedures as described in part "Affinity selection of the phage-displayed immunoreactive peptide antigens". Sequencing results can be normalized by comparing the spiked internal control serum or antibody epitope profiles between different samples. Affinity selection can be carried out in the competitive assay format where peptide-antigens binding with the respective antibody are out-competed by the addition of the free antigenic molecule.

1) One volume of the preabsorption solution (M13KE_mWT/ER2738 lysate) is mixed with two volumes of PBS. Then Tween20 (#4158, Naxo, Estonia) is added to a final concentration of 0.1%. Per each collection microtube well (19560, Qiagen, Hilden, Germany), 0.6 ml of the diluted preabsorption solution is prepared. Then, either
2) 2.5 μg monoclonal antibody is added.
   a. Optional. For assay normalization 6,25 μl protein G beads slurry saturated with internal control serum or internal control antibody is added. Beads are incubated 1 hour at room temperature with an excessive amount of serum or antibody solution and washed three times with 1 ml of PBS-0,1% Tween20 (PBS-T 0,1%).
   b. Optional. Addition of relevant amounts of the free peptide antigen or protein antigen for competition analysis.

Collection microtubes are covered with caps (19566, Qiagen) and incubated overnight at 4° C. rotating.

1-5: Affinity Selection of the Phage-Displayed Immunoreactive Peptide Antigens

Preabsorbed sera, plasma or immunoglobulin samples, preabsorbed random phage library and pretreated magnetic beads will be mixed together. Consequently, phages displaying random peptides that are able to interact with antibody paratopes are magnetically separated from the unbinding phages. The unbound phages will be removed by using multiple washing steps.

1) The collection tubes containing preabsorbed serum prepared in part "Pre-absorption of the sera, plasma or immunoglobulin samples" are centrifuged at 1000 g for 1 min.
2) Subsequently 0.3 ml of precleared phage library/magnetic beads suspension prepared in part "Pretreating magnetic beads with glycine" is added to each well.

3) Tubes are covered with fresh caps and the plate is incubated overnight at 4° C. while rotating.
4) The next day, the plate with samples is centrifuged at 1000 g for 1 min.
5) The magnetic beads are resuspended and the solution is transferred from the collection microtube to the wells of the deep well plate (4ti-0136, 4titude, Surrey, UK).
6) KingFisher Flex 96 deep well magnetic head (24074430, Thermo Scientific, MA, USA) with 96 Rod-Cover (1031668, Qiagen) is shielded and carefully inserted into the wells containing beads,
7) The beads are collected, transferred into the new deep well plate (DWP), prefilled with 1 ml of PBS-0.5% Tween 20 and resuspended until homogenous.
8) The washing cycle (starting from step 6) is repeated 5 times. Each time, a new DWP is used.
9) After the final washes, the beads are captured with deep well magnetic head of KingFisher Flex 96 and transferred into the DNA Lobind plate (0030 503.201, Eppendorf, Hamburg, Germany) prefilled with 120 μl of PBS.
10) The beads are resuspended using KingFisher Flex 96 deep well magnetic head inserted into the Lobind plate that is placed on the Invitrogen magnetic plate (120.27, Invitrogen, CA, USA).
11) Lobind plate containing phages is covered with PCR foil (4ti-0550, 4titude) and stored at 4° C. overnight.

1-6: Phage ssDNA Purification and Precipitation

Affinity selected phages are lyzed on the beads and ssDNA is purified with DNeasy® Blood &Tissue kit according to the manufacturer's instructions. Four phage clones from different 12-mer library lot that are sequence verified, quantified with phage titration ELISA kit (#PRPHAGE, PROGEN Biotechnik GmbH, Germany) and their concentrations are equalized. Respective phages serve as internal assay standards with known input copy number. A further precipitation of ssDNA is performed to concentrate the sample.

1) Preparation of lysis buffer: 200 μl of buffer AL, 20 μl of proteinase K (DNeasy® Blood &Tissue kit, #69504, Qiagen), 79 μl of PBS and 1 μl pooled internal control phages (100 particles in total).
2) 0.3 ml of lysis buffer is added into each DNA Lobind tube or well of the deep well plate and the phages attached to the beads are resuspended. The samples are incubated at 56° C. for 20 minutes.
3) Tubes/plates are spinned briefly and 200 μl of 96% ethanol is added to each sample, mixed and the beads are captured by magnet.
4) The mixture is transferred to the Qiagen DNeasy spin columns and the manufacturer's instructions are followed in obtaining the purified phage ssDNA. 55 μl of Buffer AE is used for the eluation of the phage ssDNA from the DNeasy membrane.
5) Subsequently the DNA precipitation solution is prepared with KOAc and mixed with phage ssDNA. 2.5 volumes of 96% EtOH is added and the samples are incubated overnight at −20° C. The next day, precipitated phage ssDNAs are resuspended in 25 μl mQ and stored at −20° C.

1-7: PCR Amplification of the Region Encoding Peptide-Antigens in the Genome of the Affinity Selected Phages Affinity selected phages contain in their genome a DNA region encoding peptide antigen. This DNA region is amplified by PCR. The 3' region of sense and antisense primers contains region binding with M13KE vector and 5' region of each primer contains the adapter sequence, necessary for fragment hybridization onto the Illumina chip surface (Quail MA, 2008 Supplement; Hoen PAC, 2011).

Each sample is amplified using a specific 3' primer that contains a unique, either 4 or 6 bp long barcode in the middle of the primer sequence (FIG. 1). Barcoding of each of the samples enables to run parallel sequencing of the multiple samples on a single Illumina chip lane.

1) PCR mastermix is prepared containing 1×Phusion HF buffer, 0.2 mM dNTP mix (dATP, dTTP, dGTP, dCTP), 0.5 μM phosphorothioate modified sense primer SEQ ID NO. 15: GMM_PTO_s1 (5'-AATGATACGGCGACCACCGAGATCTACACTGATCTAGTGGTACCTTTCT ATTCTCA*C*T*C*T-3'), 0.5 μM uniquely barcoded antisense primer SEQ ID NO. 16: GMM_index_as1 (5'-CAAGCAGAAGACGGCATACGAGATNNNN(NN)CC-CTCATAGTTAGCGTAACG -3'), 2U of Phusion HF Hot Start polymerase (Thermo Scientific, MA, USA), 25 μl of precipitated phage ssDNA from Section 6 and mQ up to volume of 50 μl. The N in primer sequence marks either four or six basepair (additional two basepairs are marked in parentheses) barcode position that is used in current example.
2) The following program is used for amplification:

| | Ramp temperature | Incubation time |
|---|---|---|
| 1 | 98° C. | 25 sec |
| 2 | 98° C. | 5 sec |
| 3 | 58° C. | 20 sec |
| 4 | 72° C. | 20 sec |
| 5 | | repeat steps 2-4 10× |
| 6 | 98° C. | 5 sec |
| 7 | 68° C. | 20 sec |
| 8 | 72° C. | 20 sec |
| 9 | | repeat steps 6-8 20× |
| 10 | 72° C. | 5 min |
| 11 | 15° C. | 1 min |

Control electrophoresis of PCR products is performed using a 2% weight/vol agarose TBE gel with ethidium bromide in order to verify successful amplification.

1-8: Purification of PCR Products

Purification of the amplified PCR products will remove nucleotides and unbound primers that would otherwise intervene with the high-throughput (HTP) sequencing process.

The purification is performed using QIAVac 96 system (19504, Qiagen) and QIAquick® 96 PCR purification kit (28181, Qiagen) according to the manufacturer's instructions with an exception that the columns are washed 2 times with 1 ml of buffer PE. Column bound PCR products are eluted by using 60 μl of buffer EB.

1-9: Quantification and Normalization of the MVA Library

After the purification of PCR products, the samples are quantified and normalized subsequently in order to achieve equal concentrations of each of the barcoded amplicons in the final sample pool.

1) The concentration of each purified PCR product is measured with Qubit dsDNA HS assay kit (Q32854, Invitrogen) according to the manufacturer's protocol.
2) Individual sample concentrations in the final sample pool are equalized by adjusting the amount of DNA of each of the samples respectively
3) Finally the MVA library concentration is determined with dsDNA HS assay Qubit kit.

1-10: Next Generation Sequencing Analysis

Next generation sequencing analysis is performed using Illumina Hiseq2000 or Hiseq2500 platform in a high-throughput or rapid mode (version 3 HiSeq flow cell). Standard run of with the single read length of 50 bp is performed using custom sequencing and index primers with the sequences as follows 1) phage amplicon-specific custom sequencing primer (SEQ ID NO. 17: MVA_seq_s1 5°-CGAGATCTACACTGATCTAGTGGTACCTTTCTATTCTCACTCT-3' is used to sequence the region containing the random peptide encoding DNA sequence.
2) phage amplicon-specific index primer SEQ ID NO. 18: MVA_index_s1 5'-GGAAAGACGACAAAACTTTAGATCGTTACGCTAACTATGAGGG-3' is used to sequence the barcode of the DNA sequence.

1-11: Peptide Database Generation

Illumina raw sequencing data is first demultiplexed using defined barcodes. All nucleic acid sequences are converted to peptide sequences and normalized by total counts per sample. Respective peptides are compiling a database named pep_summary. The database creation includes the following steps.

1) Obtained nucleic acid sequences are demultiplexed and counted using CASAVA software of a custom Python script.
2) Single copy sequences and sequences with no defined constant factor next to the sequence encoding the random peptide are filtered out.
3) Random peptide encoding DNA is trimmed and translated. Translation is done using the standard codon table with one exception—stop codon TAG is encoding glutamine (Q).
4) Peptide frequencies are normalized by total counts of sequences obtained per respective samples and by total counts of internal control phages added in 1-6, step 1.
5) Peptides are added to the pep_summary database.
6) fullMS database is constantly updated with new peptide sequences based on a renewed pep_summary, containing all the peptides wherein the peptide count in at least one sample is >10.
7) filterMS database is updated based on a renewed pep_summary, containing all the peptides wherein at least two unique samples, the peptide count is >10.

Example 2

Epitope Mapping of a Monoclonal Antibody

The mapping of continuous as well as discontinuous epitopes of monoclonal antibodies was carried out by using the method described in Example 1.

Materials and Methods

The epitope depth of the antibodies recognizing continuous epitopes: anti-c-myc 9E10 (M4439, Sigma Aldrich, M O, USA) and anti-FLAG M2 (F3290, Sigma Aldrich); and a discontinuous epitope, namely that of anti-MASH1 (556604, BD Biosciences, CA, USA) were analyzed in parallel using the method described in example 1-4. Also, in the competition analysis, a 100 μg FLAG peptide DYKDDDDK (SEQ ID NO. 19) or myc peptide EQKLISEEDL (SEQ ID NO. 20) was mixed with pre-absorption solution as described in example 1-4, step 2b.

Anti-c-myc 9E10 or anti-FLAG M2 titration analysis with saturated beads was performed with 5-fold serial dilution starting from 5 μg of the monoclonal antibody. Internal control beads were saturated with 2,5 μg of control sera and used in competition analysis as described in example 1-4, step 2a.

The 2_sample_comparison tool enables a quick comparison, for example of parallels, time-series of samples, competition analysis sets etc. It defines peptides that are differentially captured in respect to the defined threshold and subjects a user-defined input set of peptides for the MEME (Multiple EM for Motif Elicitation) motif-building tool (Bailey TL, 2009). The MEME output ranks the peptides for the presence of the dominant motif determinants. Identified position specific scoring matrix (PSSM) i.e. motif profile, characterizing the predicted motif are graphical visualized with WEBLOGO3. The overall height of the stack indicates the sequence conservation at that amino acid position, while the height of symbols within the stack indicates the relative frequency of each amino acid at that position (Crooks G E, 2004). Motif can also be expressed as respective consensus sequence, where single letters point to more conserved motif residues whereas in case of groups of letters in square brackets respective substitutions are tolerated.

1) Peptides with the frequency of occurrence (counts) above the defined threshold, that are present in the case sample and absent in the control were filtered out from the "fullMS" or "pep_summary" database constructed in example 1-12 and sorted based on the counts.
2) User defined sets of peptides with the highest counts were subjected to MEME motif analysis program. Motif range was defined to be between 3-12 residues and ZOOPS (Zero Or One Motif Per Sequence) the analysis mode used was default.
3) Summarized counts of the all peptides belonging to the specific motif were visualized in the reference samples that were specified by the user.

Results

Determination of the Depth (Total of Epitope Variants Recognized) of the Anti-c-Myc 9E10 Antibody MVA profiling of anti-c-myc 9E10 was carried out. This antibody clone has previously been shown by others to have a minimal epitope with sequence of SEQ ID NO. 21: L[I/L/V] [S/A/G/P] [E/F/M/Q]XX[L/V] (Hilpert et al 2001), where residues in positions marked with X could be substituted by any amino acid.

2_sample_comparison tool defined 200 peptides that were at least 10 times downregulated in the competition analysis using the synthetic peptide SEQ ID NO. 20: EQKLISEEDL for the anti-c-myc 9E10 antibody binding. Identified core motif of anti-c-myc 9E10 recapitulated fully the key positions and also the depth of the epitope that were previously defined by Hilpert et al (FIG. 3).

Referring to FIG. 3, the core motif of anti-c-myc 9E10 is visualized as PSSM (position specific scoring matrix). 200 peptides that were the most downregulated upon the competition analysis with EQKLISEEDL peptide (SEQ ID NO. 20) (shown below the core motif), were subjected to 2_sample_comparison analysis. The core motif was found to be present in 98% (n=196) of the analyzed peptides.

Identification of the Minimal Epitope of FLAG-M2 Monoclonal Antibody

MVA was performed as described in the Example 1 using the anti-FLAG M2 antibody raised against the linear peptide DYKDDDDK (SEQ ID NO. 19). Upon the analysis, the defined minimal epitope with the sequence YK..D (FIG. 4) recapitulated fully the core motif that was obtained when a 7-mer random peptide phage library was subjected for three rounds of biopanning (NEB Technical Bulletin #E8100, E8110, E8120 (12/2/06)).

Figure 4:
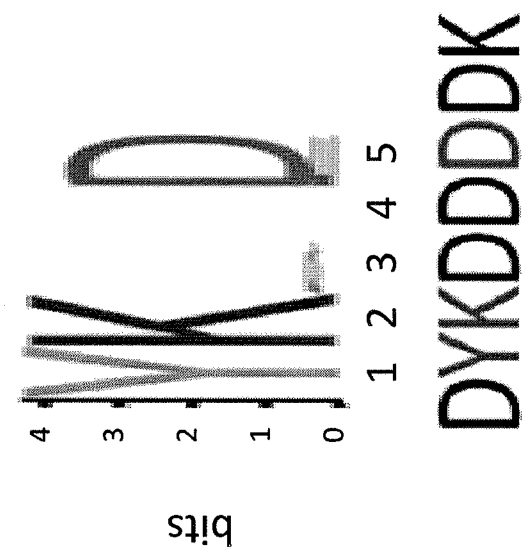
FIG. 4 depicts results revealing that 2000 most frequent peptides were downregulated upon competition analysis with peptide DYKDDDDK (SEQ ID NO. 19). The sequence of the minimal motif YK..D was found to be present in 99,6% (n=1992) of the peptides

Referring to FIG. 4, 2_sample_comparison analysis revealed that 2000 most frequent peptides were downregulated upon competition analysis with peptide DYKDDDDK (SEQ ID NO. 19). The sequence of the minimal motif YK..D was found to be present in 99,6% (n=1992) of the peptides.

Peptides with High Frequency of Selection Contain a-Well Preserved Motif

Recent data demonstrated that three rounds of affinity selection using FLAG M2 antibody yielded in the exclusively DYK..D (SEQ ID NO. 4) motif carrying peptide-antigens (Srila and Yamabhai, 2013).

Figure 5:
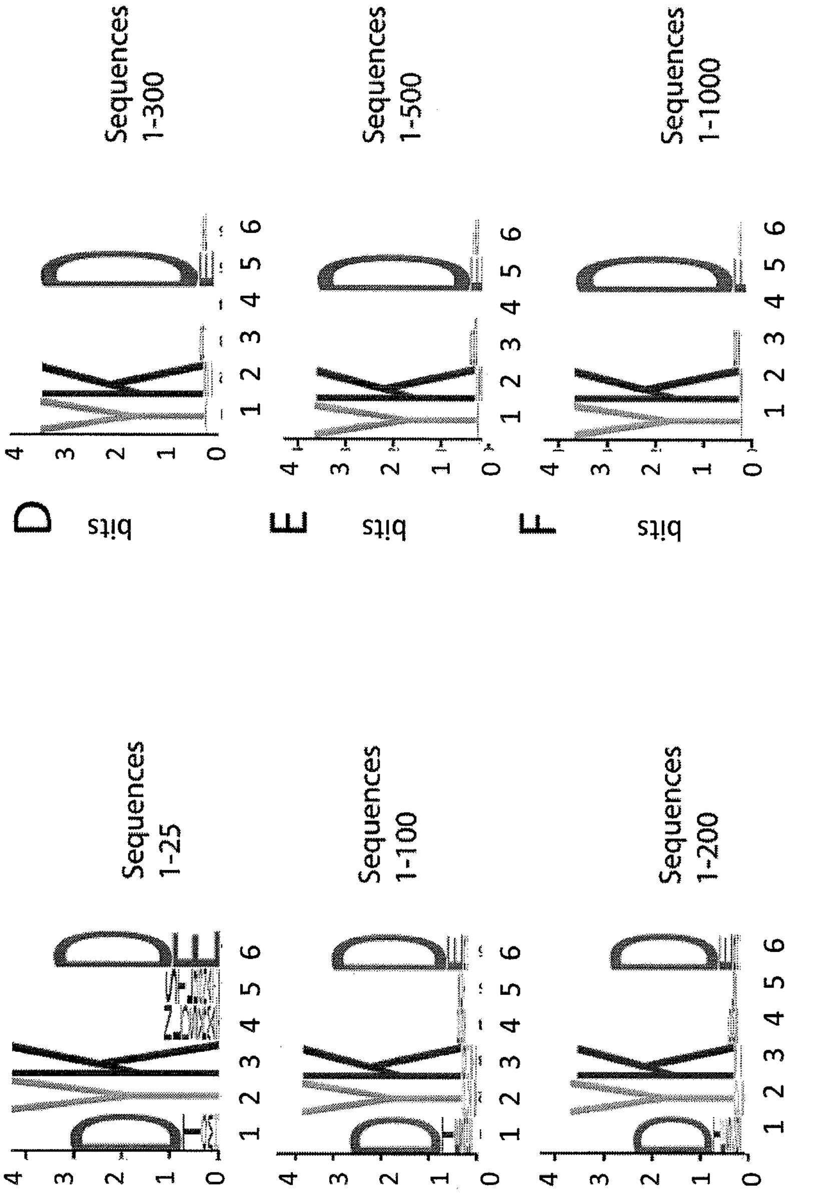
FIG. 5 depicts results from analysis of peptides with high counts contain extended FLAG M2 motif DYK..D (SEQ ID NO. 4). Two thousand unique peptides containing FLAG M2 minimal motif were ranked according to their frequency of occurrence. Top 25, 100, 200, 300, 500 or 1000 peptides were subjected to MEME, respective motifs obtained are presented in panels A-F, respectively.

If for MEME analysis peptides were selected amongst the frequently observed peptides, then the DYK..D (SEQ ID NO. 4) extended motif was identified as the one recognized by the FLAG M2 antibody. Therefore a conclusion was made that when the data analysis includes peptides with higher counts of frequency, then the first aspartic acid (D) in the epitope motif of the FLAG M2 is not essential and the minimal motif is composed of only three amino acids (FIG. 5). This is a clear indication of the high diversity of the 12-mer NEB library allowing the competition between phages presenting optimal and suboptimal motifs. Considering that the phage library contains a high number of peptide sequences containing a unique minimal motif, it is likely that one could define simultaneously by using MVA a minimal core motif and extended motifs.

Mapping of a Discontinuous Monoclonal Antibody Epitope

Figure 6:
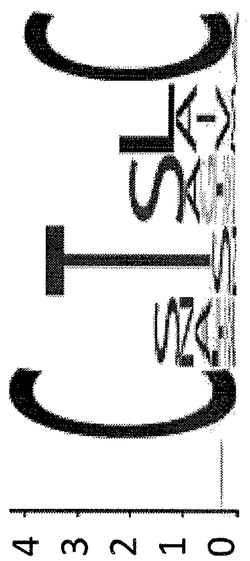
FIG. 6 depicts results of the discontinuous motif recognized by the anti-MASH1 antibody as identified by MVA. The minimal motif that is flanked by two conserved cysteins was found to be present in 44% (n=88) of the peptides when 200 most frequent peptides were subjected to MEME analysis.

MVA profiling of anti-MASH1 (556604, BD Biosciences) monoclonal antibody was carried out. anti-MASH1 is raised against the full-length rat MASH1 protein and the detailed epitope is not known. Upon MVA, 200 most frequently selected peptides were analyzed using MEME and 44% (n=88) of them were found to contain a motif that was flanked with two conserved cysteins (FIG. 6).

Majority of the other frequent peptides subjected to MEME analysis were identified as high frequency peptides specific to the spiked-in internal control serum as described in example 1-4, step 2a.

Titration of Anti-Myc and Anti-FLAG Monoclonal Antibodies

Figure 7:
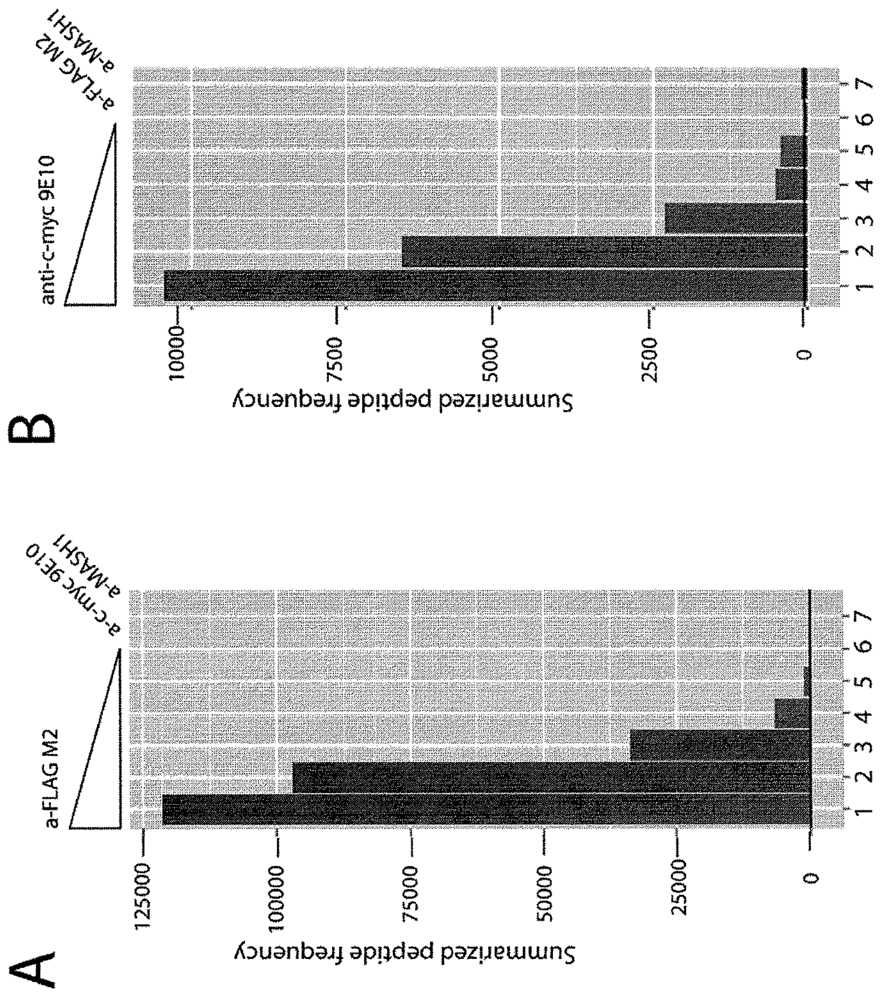
FIG. 7 depicts anti-c-myc 9E10 (panel A) and anti-FLAG M2 (panel B) signature carrying, the most frequently observed 200 peptides were still detected with 78 fold molar excess of the internal control sera (lane 5). No signal was observed with negative controls (lanes 6-7).

Anti-Myc or anti-FLAG antibody saturated beads, respectively, were titred with the internal control serum saturated beads. MVA data was analyzed by counting the 200 most frequent peptides that contained respective minimal motifs. According to the analyses, the signature of respective peptides was still detectable in the competition assay with the addition of the 78-fold molar excess of the internal control beads (FIG. 7).

REFERENCES

Hilpert K, Hansen G, Wessner H, Kiittner G, Welfle K, Seifert M, Hôhne W. Anti-c-myc antibody 9E10: epitope key positions and variability characterized using peptide spot synthesis on cellulose. Protein Eng. 2001 October; 14(10):803-6.

Srila W, Yamabhai M. Identification of amino acid residues responsible for the binding to anti-FLAG™ M2 antibody using a phage display combinatorial peptide library. Appl Biochem Biotechnol. 2013 October; 171(3):583-9.

Bailey T L, Boden M, Buske F A, Frith M, Grant C E, Clementi L, Ren J, Li W W, Noble W S. MEME SUITE: tools for motif discovery and searching. Nucleic Acids Res. 2009 July; 37(Web Server issue):W202-8.

Crooks G E, Hon G, Chandonia J M, Brenner S E. WebLogo: a sequence logo generator. Genome Res. 2004 June; 14(6):1188-90.

Example 3

Validation of Linear and Conformational Epitopes

For validation of MVA analysis provided as example 2, phage/protein array technology was used along with immunoassay using anti-FLAG M2, anti-c-myc 9E10 or anti-MASH1 antibodies. Peptides containing FLAG or myc-specific motifs showed specific interaction with respective antibodies, as expected. In addition, Alanine substitution analysis was used to demonstrate the specificity of the anti-MASH1 discontinuous epitope motif-containing peptides.

Materials and Methods

FLAG (DYKDDDDK) (SEQ ID NO. 19) and myc (EQKLISEEDL) (SEQ ID NO. 20) peptide encoding sequences were inserted at the N-terminus of the pIII of the M13KE phage in parallel with other MVA identified peptides. HEK293 cells were transfected with the expression vector encoding human MASH1 (Uniprot P50553) or mock vector. HEK293 cell lysates were prepared in mild non-reducing conditions in order to preserve the confirmation of the native protein. Purified phages and cell lysates were printed in duplicates on ONCYTE® NOVA 16 pad nitrocellulose slides (505016, Grace Bio-Labs, OR, USA) using SpotBot®2 Personal Microarrayer (Arrayit Corporation). Fluorospot assay was performed with respective primary and secondary anti-mouse antibodies conjugated with Cy3 dye (115-165-062, Jackson ImmunoResearch, PA, USA). Slides were scanned with Ettan Digeimager (GE Healthcare, Little Chalfont, UK) and the signal was quantified using Image Quant 8.1 software.

Results

1. Validation of the Motif Recognized by Anti-c-Myc 9E10 Monoclonal Antibody.

Figure 8:
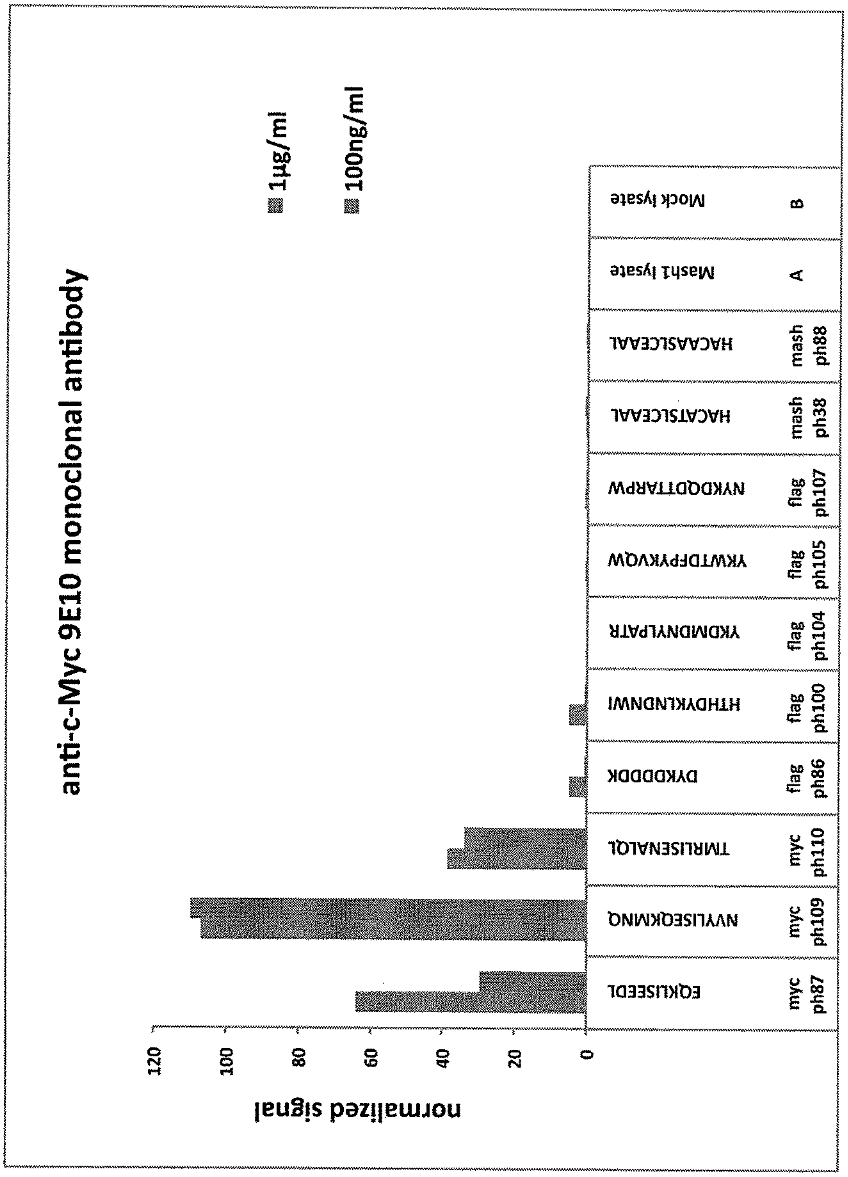
FIG. 8 depicts a graph demonstrating validation of the MVA defined-motifs as specific antigenic sequences for anti-c-myc 9E10 monoclonal antibody.

Phage array data confirmed the binding specificity of anti c-Myc 9E10 monoclonal antibody with phage PC87 presenting myc tag with the sequence EQKLISEEDL (SEQ ID NO. 20) on the surface (FIG. 8). In addition, specific binding of anti c-Myc 9E10 monoclonal antibody with MVA identified PC109 and PC110 peptides that contained the core motif LISE..[L/M] (SEQ ID NO. 22) of myc was also observed. As controls, only background signal was observed in case of fluospot analysis of phages encoding motifs similar to FLAG or MASH1 peptide antigens or cell lysates transfected with the plasmid encoding human MASH1 protein.

2. Validation of the Motif Recognized by Anti-FLAG M2 Monoclonal Antibody

Figure 9:
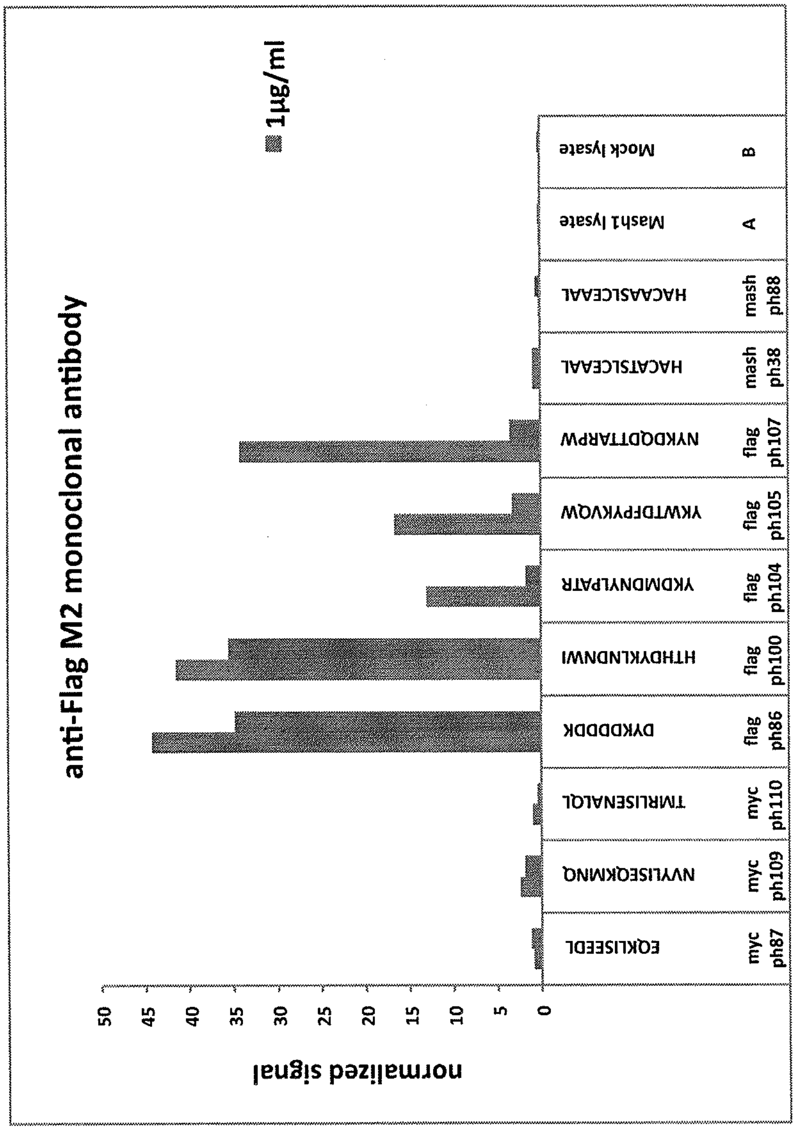
FIG. 9 depicts a graph demonstrating validation of the motif recognized by anti-FLAG M2 monoclonal antibody.

Results confirmed the binding specificity of anti-FLAG M2 monoclonal antibody with phage PC86 presenting FLAG tag DYKDDDDK (SEQ ID NO. 19)(FIG. 9). In addition, strong binding of anti-FLAG M2 monoclonal antibody with MVA-identified PC100 peptide was also observed. As expected, PC100 peptide, containing FLAG motif sequence DYK..D (SEQ ID NO. 4), allowed antibody binding with a relatively higher affinity as compared to PC104, PC105 and PC107 phages that contained minimal FLAG motif with the sequence YK.D. Only background signal was detected when phages encoding motifs identified from myc and MASH1 MVA analysis or cell lysates, transfected with plasmid encoding human MASH1 protein, were used as controls.

3. Validation of the Motif Recognized by Anti-MASH1 Monoclonal Antibody.

Figure 10:
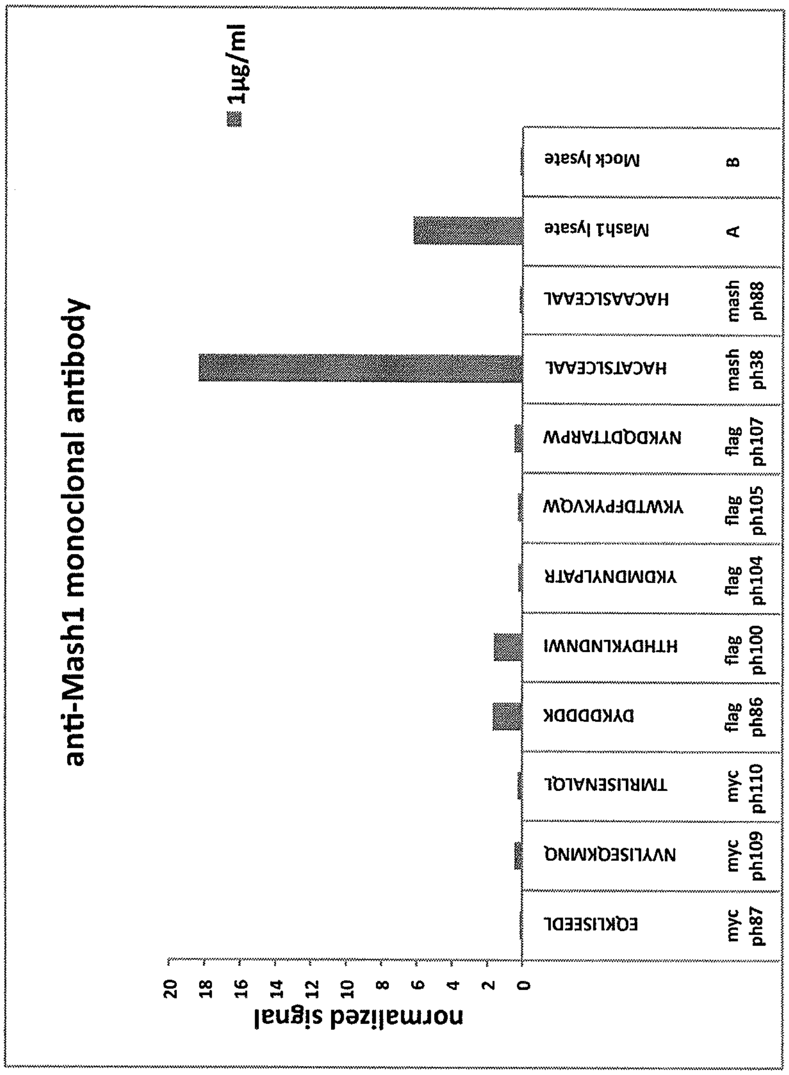
FIG. 10 depicts a graph demonstrating validation of the motif recognized by anti-MASH1 monoclonal antibody. Specifically.

Fluospot analysis confirmed the binding of anti-MASH1 monoclonal antibody with the phage PC38, presenting a peptide with the sequence SEQ ID NO. 20: HACATSLCEAAL (FIG. 10). Replacement of conserved threonine (T) with alanine (A) in the identified MASH1-specific motif with the sequence C..T.C abolished the binding of anti-MASH1 monoclonal antibody by the motif. Compared with the mock transfected HEK293 cells, lysates transfected with the construct encoding human MASH1 also showed anti-MASH1 monoclonal antibody-specific binding.

Example 4

Mapping of the Depth and Breadth of a Polyclonal Antibody

Most of the commercially available antibodies are polyclonal i.e. they are mixtures of monoclonal antibodies that recognize different epitopes of the same antigen. It has been reported that most of the antigen (immunogen) sequence is "epitope silent", such that only some regions of the antigen are able to induce a strong polyclonal immune response (Hjelm et al 2010). A fundamental limitation of the overlapping peptide array is that it cannot distinguish between overlapping monoclonal epitopes (Buus et al 2012). Data presented in example 4 show that MVA described in the Example 1 can define multiple overlapping motifs with distinctive characteristics.

Material and Methods

Affinity selection, sequencing and data preprocessing was performed as described in the Example 1, with the exception that 2.5 μg of rabbit polyclonal anti-Musashi-1 antibody (AB5977, Millipore, MA, USA) was added as an antibody for affinity selection in part 4, step 2.

Also, synthetic peptide SEQ ID NO. 30: APQPGLASPDSPHDPCK used for generation of anti-Musashi-1 antibody, was added for competition analysis in Example 1-4, step 2b.

Bioinformatic motif identification was performed using the 2_sample_comparison tool and MEME algorithm as described in the Example 2.

Results

Figure 11:
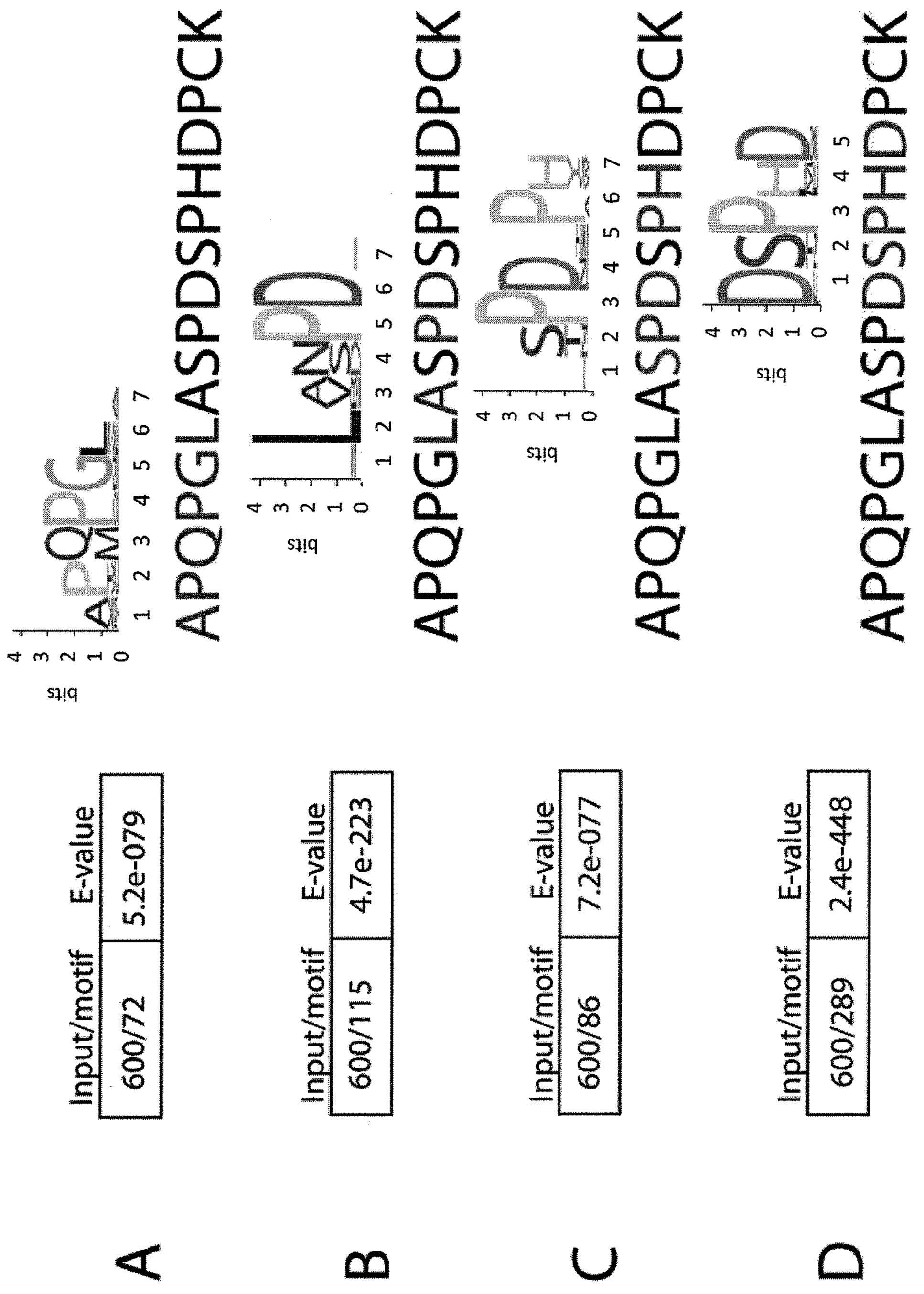
FIG. 11 depicts a table of results from epitope profiling of the polyclonal anti-Musashi-1 antibody, which defines four distinctive overlapping motifs. A) Motif A with regular expression (AP[QM]PGLA) (SEQ ID NO. 23) is spanning residues 1-6; B) Motif B (L[AV][NS]PD) (SEQ ID NO. 24) is spanning residues 6-10; C) motif C ([ST]PDxPH) (SEQ ID NO. 25) is spanning residues 8-13; D) motif D (DSPHD) (SEQ ID NO. 26) is spanning residues 10-14.

Anti-Musashi-1 polyclonal antibody was raised against a synthetic peptide covering amino acids 5-21 of Musashi protein conserved in human, mouse and rat. Analysis of 600 peptides that were most downregulated upon competition with free peptide resulted in the identification of four overlapping motifs with distinctive characteristics (FIG. 11).

Motif A (AP[QM]PGLA) (SEQ ID NO. 23), spanning residues 1-6 overlaps with motif B (L[AV][NS]PD) (SEQ ID NO. 24) spanning residues 6-10, regarding the leucine (L) in position 6.

Other motifs described, motif C ([ST]PDxPH) (SEQ ID NO. 25) spanning residues 8-13 and motif D (DSPHD) (SEQ ID NO. 26) spanning residues 10-14, also overlap with motif B. Analysis data showed that only the aspartic acid (D) in the position 10 is shared between all three respective motifs. There are clearly residues where the requirement for the presence of a defined amino acid is different. For example serine (S) in position 10 is a part of the motif D but is not present in case of motif B and motif C. Vice-versa, proline (P) in position 9 is not necessary for binding of the peptides containing motif D, but is required binding determinant of the peptides containing motif B and motif D.

Substitution analyses experiments have shown that epitope may contain highly stringent, more relaxed and nonselective positions and have a generally well-defined and sharply demarked borders (Buus S, 2012). It is highly likely that overlapping motifs B, C and D represent epitopes of three monoclonal antibodies raised against the immunodominant region of the antigen.

REFERENCES

Buus S, Rockberg J, Forsstrom B, Nilsson P, Uhlen M, Schafer-Nielsen C. High-resolution mapping of linear antibody epitopes using ultrahigh-density peptide microarrays. Mol Cell Proteomics. 2012 December; 11(12):1790-800.

Hjelm B, Fernández C D, Lofblom J, Ståhl S, Johannesson H, Rockberg J, Uhlén M. Exploring epitopes of antibodies toward the human tryptophanyl-tRNA synthetase. N Biotechnol. 2010 May 31; 27(2):129-37.

Example 5

Stablishing Antibody Meta-Profile Containing Metadatabase

Introduction

Because of the vast amount of immunoglobulins in the sera sample, generally several rounds of affinity selections are carried out using conventional phage display analysis to reduce the complexity of the data analysis (Ryvkin et al 2012). However, this leads to the overrepresentation of the peptide-antigens that react with the most prevalent antibodies. Furthermore, several rounds of intrinsic growth or amplification advantage of individual phage clones leads to antibody-independent peptide enrichment biases (Matochko et al 2012). In Example 5, an extraction of biological information from peptide database constructed in Example 1 was performed. Also, a population wide serum B-cell epitope profile database serving as a resource for group, class, family or single organism (individual) specific biomarker discovery was constructed.

Materials and Methods

Samples were prepared as described in Example 1, except in part 4, step 2 for each individual sample 2 μl of respective serum was added instead of the monoclonal antibody.

Peptide profiles derived from 742 human individual sera present in database filterMS, generated in Example 1, part 11 were selected for Motif_Summary database construction. Clustering was started with the query peptide defined by the highest count in filterMS database. Peptides that were most similar with the query peptide based on sequenced peptide counts were clustered (initial cluster). The initial cluster was aligned with MEME and a motif in the aligned cluster was defined (initial motif). All peptides from the full MS database containing initial motif were identified using FUZZPRO. The FUZZPRO output was filtered to remove all peptides that do not match with the initial cluster count pattern and final cluster was defined. Peptides that form the final cluster were removed from filterMS. Next query peptide from the filterMS file was selected. After clustering, average vector from 20 most frequently observed peptides taken from each cluster was calculated and added to Motif_Summary metadatabase. MEME was used for identification of the motif present in most frequent peptides.

Results

Figure 12:
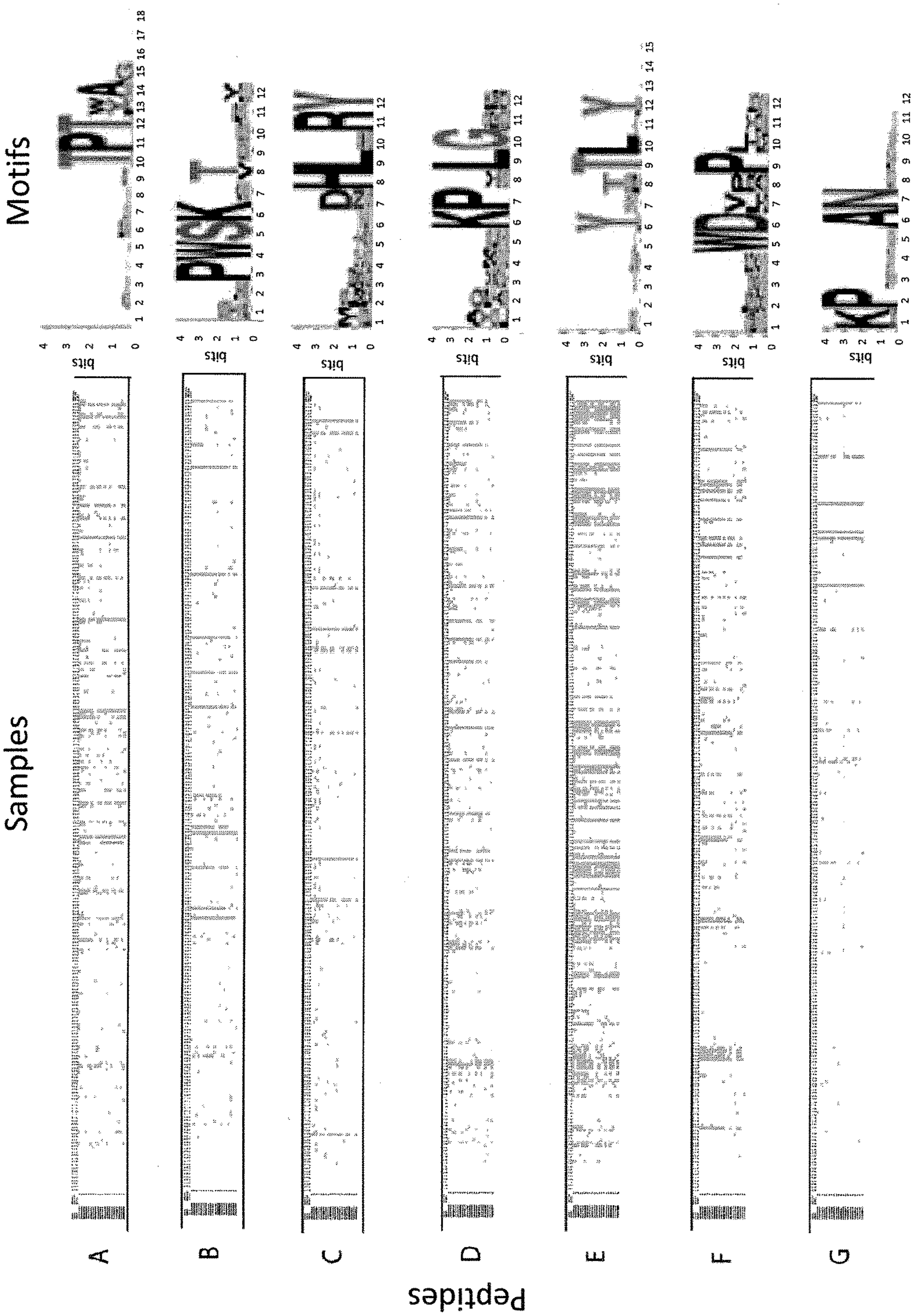
FIG. 12 depicts distinctive peptide frequency patterns define Motif summary clusters (panels A-G). Meta-profiles from 20 most frequently observed peptides from each identified cluster were generated as classificator of seroreactivity.
Figure 13:
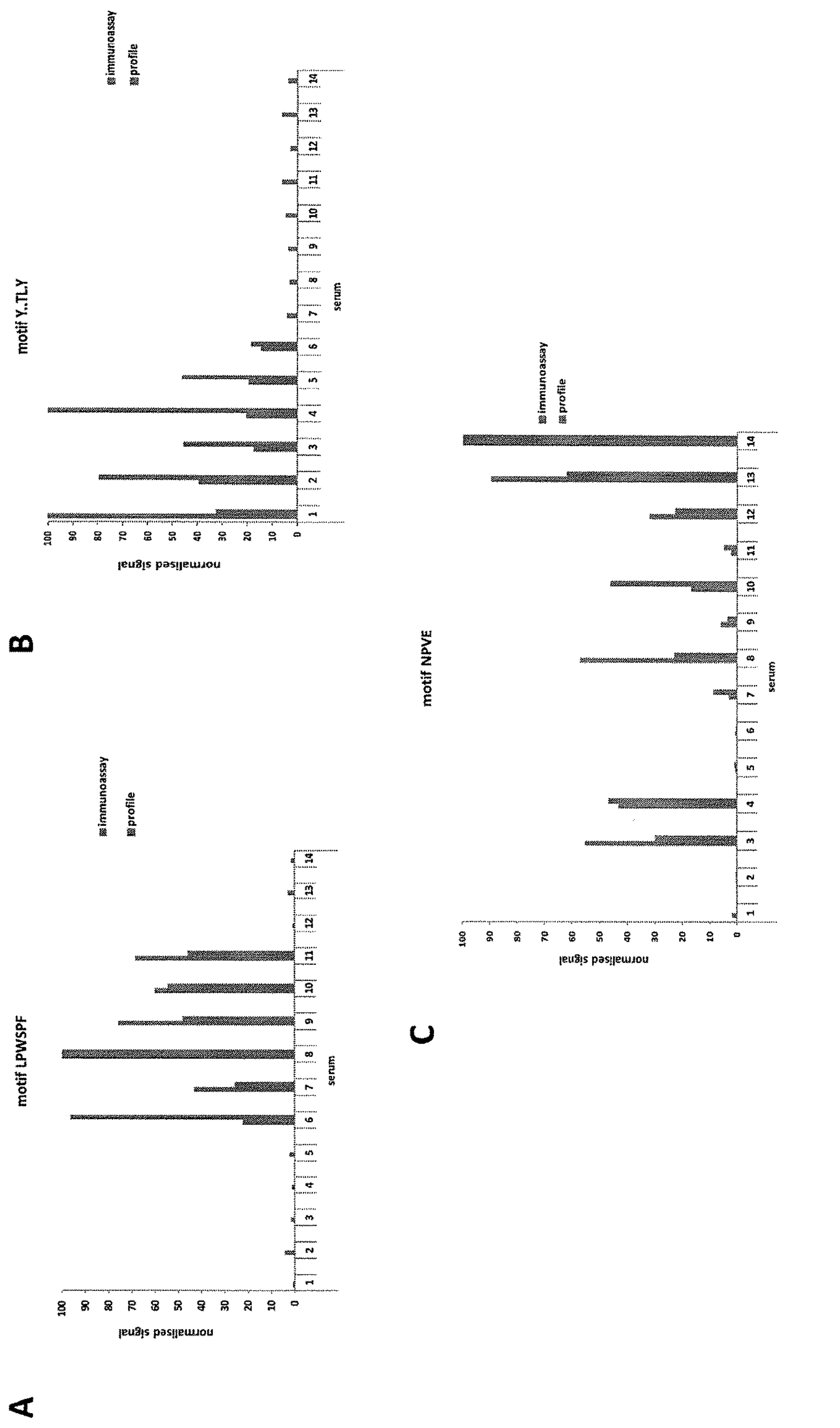
FIG. 13 depicts validation of three unique motif Y..TL.Y, LPWSPF and NPVE containing peptides on immunoassay fully recapitulated the the observed partially overlapping meta-profile signal.

Metadatabase Motif_Summary containing the identified Antibody Activity Profiles was constructed. In total, 24% of peptides from the full MS database (containing 1945919 peptides) were clustered into 1432 clusters ranging from 5 to 4000 unique peptides (FIG. 12). As observed in case of FLAG M2 analysis presented in Example 2, peptides in specific cluster with the highest count of frequency were found to contain extended motif (data not shown). Therefore average vectors of 20 most frequently observed peptide counts were selected as a classificator of seroreactivity.

Three in-silico defined peptides representing the most frequently observed peptide from three independent meta-profile cluster identified were inserted at the N-terminus of the pIII of the M13KE phage and analyzed in immunoassay. Motif Y..TL.Y (SEQ ID NO. 5) containing peptide (ELEKAYKTTLSY (SEQ ID NO. 40)), motif LPWSPF (SEQ ID NO. 29) containing peptide (SNVLPWSPFGST (SEQ ID NO. 42)) and N-terminal motif NPVE containing peptide (NPVERHLWHPLM (SEQ ID NO. 41)) encoding sequences recapitulated the peptide frequency patterns describing meta-profile behavior for 14 unique serum samples analyzed.

REFERENCES

Matochko W L, Chu K, Jin B, Lee S W, Whitesides G M, Derda R (2012) Deep sequencing analysis of phage libraries using Illumina platform. Methods. 58(1):47-55.

Ryvkin A, Ashkenazy H, Smelyanski L, Kaplan G, Penn O, Weiss-Ottolenghi Y, Privman E, Ngam P B, Woodward J E, May G D, Bell C, Pupko T, Gershoni J M (2012) Deep Panning: steps towards probing the IgOme. PLoS One. 7(8):e41469.

Sompuram S R, Bastas G, Vani K, Bogen S A (2008). Accurate identification of paraprotein antigen targets by epitope reconstruction. Blood. 111(1):302-8.

Example 6

Establishing Antibody Activity Profile in a Biological Sample Infected by Pathogen Motif_Summary database was screened and multiple motifs specific to Human Cytomegalovirus (HCMV) were identified.

Materials and Methods

For sample biological preparation protocol in Example 1 was used, with an exception in part 4, step 2, where 2 μl of individual serum sample was used instead of monoclonal antibody. Serum B-cell epitope profile database covering the Antibody Activity Profiles of human samples was constructed in Example 5. HCMV seropositivity of the patients and controls was determined clinically (Tartu University Hospital United Laboratories, Estonia).

In order to obtain differentiating motifs Motif Summary database was analyzed with 2_group_comparison tool. Differentially expressed motifs in user defined case and control group were defined and average counts of the 20 most frequent peptides from each cluster were visualized.

Differentially expressed profiles were selected for further analysis with motif combination tool. Motifs covering as many cases and as few controls as possible were found. The main steps of motif combination tool were:

1. All possible motif+threshold pairs were constructed and ones selected that were biased to cases.

All motif counts from provided cases were taken as possible thresholds for a motif. A sample was considered positive in a motif-threshold pair when it count in the motif was greater than or equal to the motifs threshold. Positive and negative samples among cases and controls were counted and those motif-threshold pairs that were not significantly better than random by using Fisher's exact test, discarded.

2. K-out-of-M combinations were constructed with M motifs where a sample was considered positive when it was positive in at least K of these M motifs. Bottom-up approach was used to build these combinations. Each K-out-of-M combination (where K<M) was expanded to K-out-of-(M+1) and each M-out-of-M combination was expanded to M-out-of-(M+1) and (M+1)-out-of-(M+1) combination. To construct out-of-(M+1) combinations, best 20 combinations from each sensitivity level in out-of-M combinations were chosen.

Figure 14:
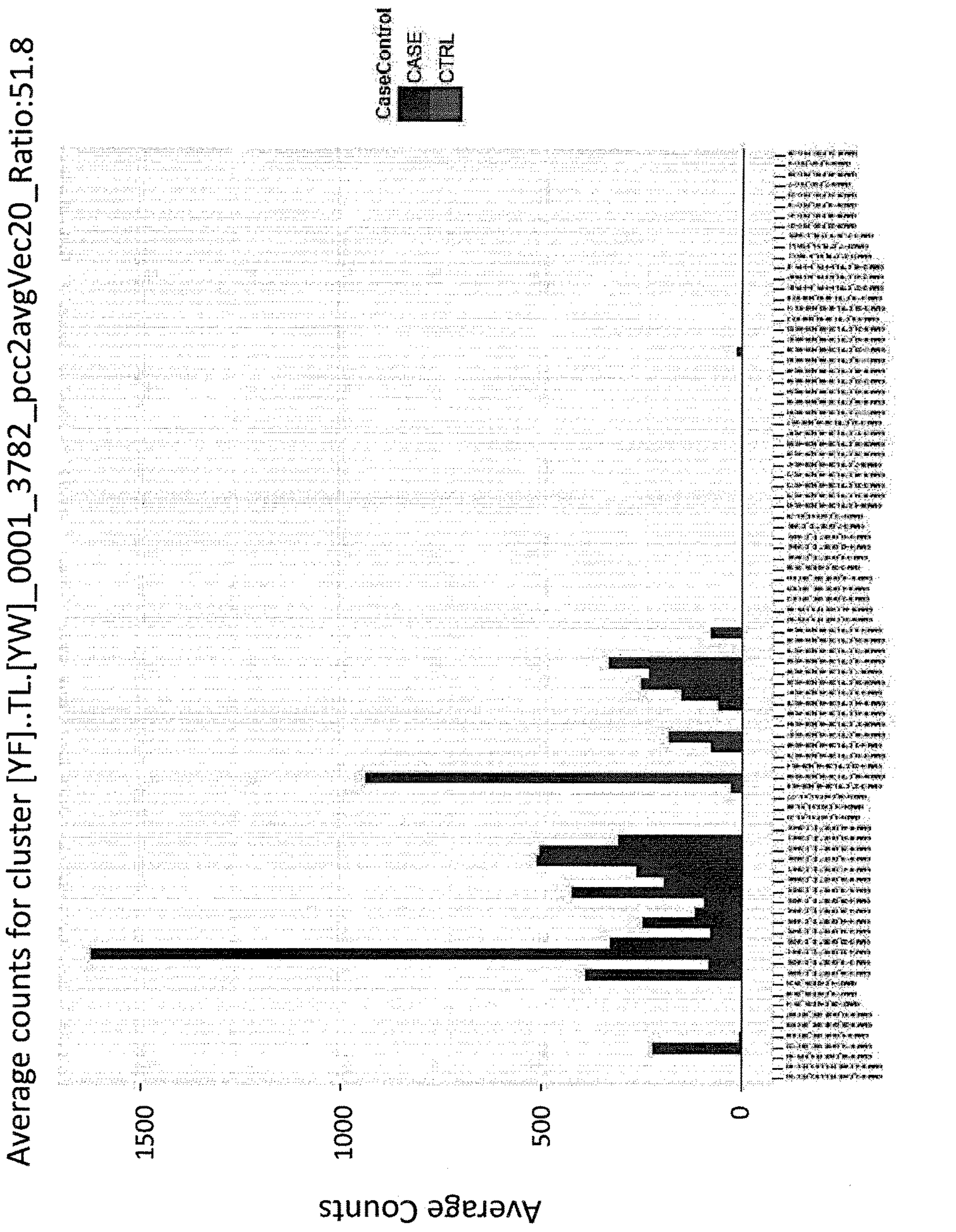
FIG. 14 depicts average counts of 20 most frequently observed peptides from cluster defined by motif [YF]..TL.[YW] (SEQ ID NO. 32). HCMV (SEQ ID NO. 33) seropositive (CASE) and seronegative (CTRL) samples were analyzed.

3. Best combinations were selected. Out-of-M combinations that have the same sensitivity as out-of-m combinations (m<=M) but worse specificity were discarded Results Clinically verified HCMV (SEQ ID NO. 33) seropositive and seronegative samples were analyzed with the 2_group_ comparison tool and motif [YF]..TL.[YW] SEQ ID NO. 32) composed of 3782 unique peptides was found to be most enriched toward cases (FIG. 14). Respective motif has been described in the literature as epitope AD-2S1 located on the envelope glycoprotein B of HCMV (SEQ ID NO. 33) (Sompuram et al 2008). Motif [YF]..TL.[YW] (SEQ ID NO. 32) had a sensitivity of 57% and specificity of 100%, however, when six other motifs were selected with motif combination tool sensitivity of the motif set raised to 95% and specificity was 98% (FIG. 15).

In FIG. 14, The average counts of 20 most frequently observed peptides from cluster defined by motif [YF]..TL.[YW] (SEQ ID NO. 32). HCMV (SEQ ID NO. 33) seropositive (CASE) and seronegative (CTRL) samples were analyzed.

Figure 15:
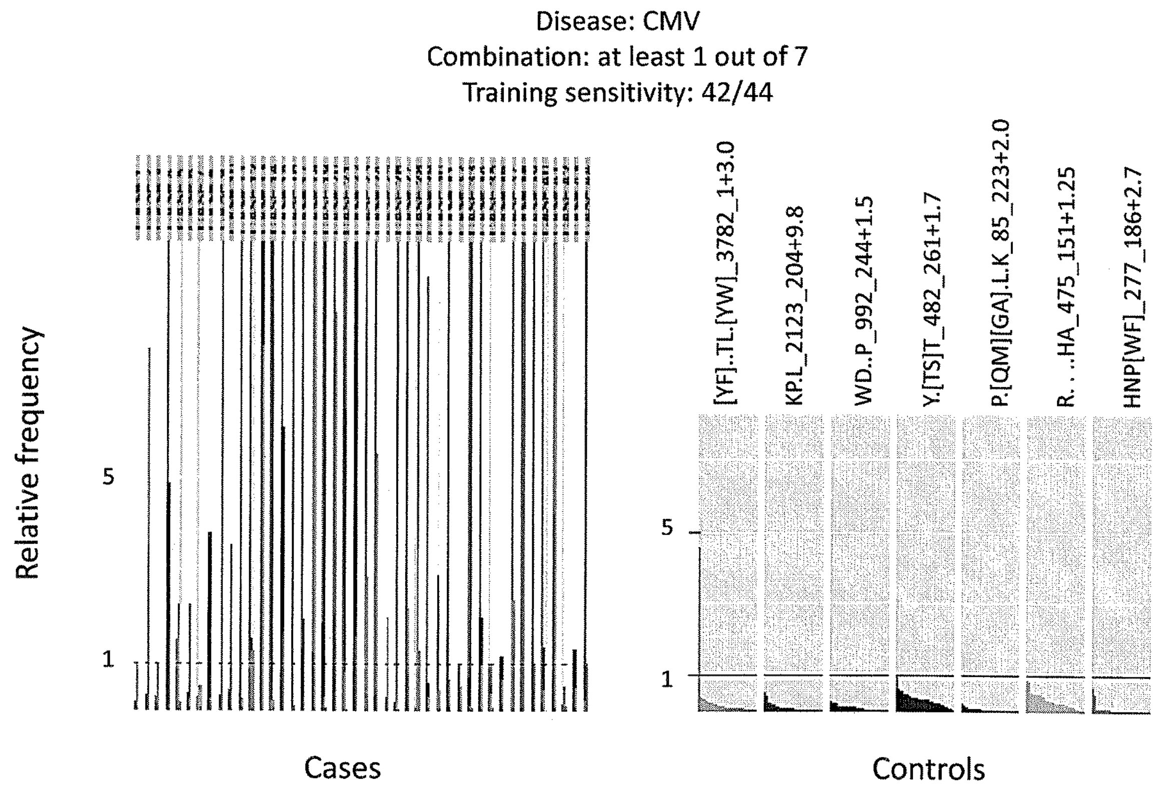
FIG. 15 depicts HCMV (SEQ ID NO. 33) motif combination identified with motif combination tool. Combination of motifs covered the HCMV (SEQ ID NO. 33) seropositive samples with 95% specificity and 98% specificity.

In FIG. 15, HCMV (SEQ ID NO. 33) motif combination identified with motif_combination tool. Combination of motifs covered the HCMV (SEQ ID NO. 33) seropositive samples with 95% specificity and 98% specificity.

REFERENCES

Matochko W L, Chu K, Jin B, Lee S W, Whitesides G M, Derda R (2012) Deep sequencing analysis of phage libraries using Illumina platform. Methods. 58(1):47-55.

Ryvkin A, Ashkenazy H, Smelyanski L, Kaplan G, Penn O, Weiss-Ottolenghi Y, Privman E, Ngam P B, Woodward J E, May G D, Bell C, Pupko T, Gershoni J M (2012) Deep Panning: steps towards probing the IgOme. PLoS One. 7(8):e41469.

Sompuram S R, Bastas G, Vani K, Bogen S A (2008) Accurate identification of paraprotein antigen targets by epitope reconstruction. Blood. 111(1):302-8.

Example 7

Generation of a Vaccination Profile from Epitope Mapping

The immune response to vaccination is likely to be influenced by genotype. Accordingly, twin and sibling studies have shown heritability estimates as high as 45% for a varicella vaccine (Klein et al 2007) and 90% for the measles vaccine (Tan et al 2001). Studies investigating influenza vaccine immunogenicity in humans have consistently shown large inter-individual variability. But the contribution of other than the genetic contribution to this variability remains poorly understood. Data presented in Example 7 show that MVA described in the Example 1 can identify vaccine-specific peptide-antigen profiles with distinctive characteristics of individual specificity.

Materials and Methods

Serum samples were collected from patients immunized with HPV subtype specific vaccines Cervarix or Silgard (Gardasil). Biopanning, sequencing and data preprocessing was performed as described in the Example 1, with the exception that vaccine was added for competition as described in the Example 1 (part 4, step2b) and 2 μl of serum sample was used in part 4, step 2 instead of monoclonal antibody.

2_sample_comparison tool described in Example 2, was used for quick comparison of vaccination time points and competition experiments. Vaccination profiles were generated by comparing the pre-immune sera with the sera from the first and last time points of vaccinations.

Results

Figure 16:
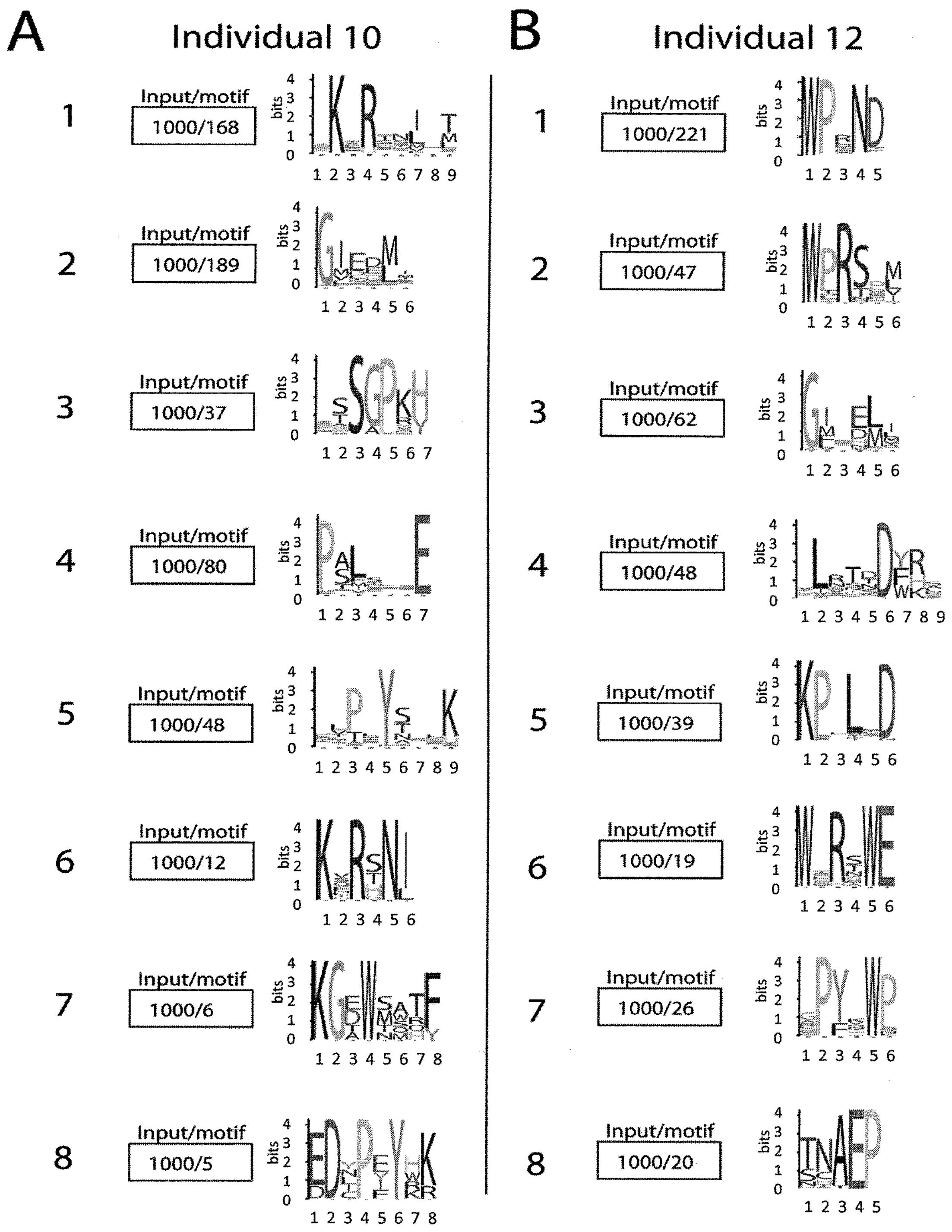
FIG. 16 depicts vaccine-induced motifs shared amongst different individuals epitope profiles. Highly similar minimal motifs composed of overlapping sets of peptides were identified among the individual specific motifs when vaccine-induced profiles were compared. N-terminal motif with the sequence of GIED[ML] (SEQ ID NO. 34) was common for individual 10 (motif 2) and individual 12 (motif 3) when MVA identified vaccine induced profiles were compared.

Analysis of the 1000 most differentially recognized peptide-antigens with 2_sample_comparison tool, a vast set of individual specific epitope motifs constituting the immune system's response to vaccination was identified. Most epitope motif sequences did not align with the HPV L1 protein linear sequence, indicating that they mimic conformational epitopes (data not shown). Among the individual specific motifs, almost identical epitopes could be found, referring that the immune response has been directed against the same epitopes of the antigen (FIG. 16).

REFERENCES

Klein N P, Fireman B, Enright A, Ray P, Black S, Dekker C L (2007) Clinical Immunization Safety Assessment Network. A role for genetics in the immune response to the varicella vaccine. Pediatr Infect Dis J. 26(4):300-5.

Tan P L, Jacobson R M, Poland G A, Jacobsen S J, Pankratz V S (2001) Twin studies of immunogenicity—determining the genetic contribution to vaccine failure. Vaccine. 19(17-19):2434-9.

Example 8

Forming Antibody Activity Profile and Epitope Profile for Biological Sample Diagnosed with HPV Cervical Cancer The immune system is a key mechanism to fight diseases. Profiling of the activity of the antibodies (binding to antigens) enables to develop novel diagnostic tools for a variety of diseases and conditions. A workflow was developed to identify and monitor the global activity of immunoglobulins. The immunome profiling, however, would be to rapidly assess the spectrum of different health conditions that have a reflection in the antibody profiles.

The antibody response to HPV is virus subtype-specific, and profiling of the global antibody activity would contribute to determining of the spread of type-specific HPV infections in populations, monitoring of the effect of HPV vaccines in inducing protective antibodies, but most of all to evaluation of oncogenic threat of the infection. The antibody response to HPV is complex since infection and disease lead to distinct virus subtype-specific antibody responses. At present there is no clinically useful serological assay of HPV exposure or susceptibility. MVA enables to identify biomarkers for cervical cancer pre-cancerous changes from blood sera.

Materials and Methods

The serum samples were from patients with defined dysplasia: 3 CIN1 patients, 28 CIN2 patients, 15 CIN3 patients and 2 Carcinoma in situ, in total 53 samples. 70 donor serum samples were used as a control. Additionally, pre- and post-vaccination sera of 14 individuals, vaccinated with Cervarix or Gardasil, were included to identify the seroreactivity profiles against HPV L1 capsid proteins. These serum probes were prepared and analyzed before first vaccination, before the second vaccination, before the third vaccination and after the third vaccination. Also several hundred samples from patients with different diagnoses were included in the study.

A clinical study was performed to identify and validate peptide mimotopes for HPV-associated cervical cancer diagnostics. Sera from different study groups were analyzed using antibody profiling method described in the Example 1, with serum used as a source of affinity binding of IgG antibodies in part 4, step 2.

Results

Figure 17:
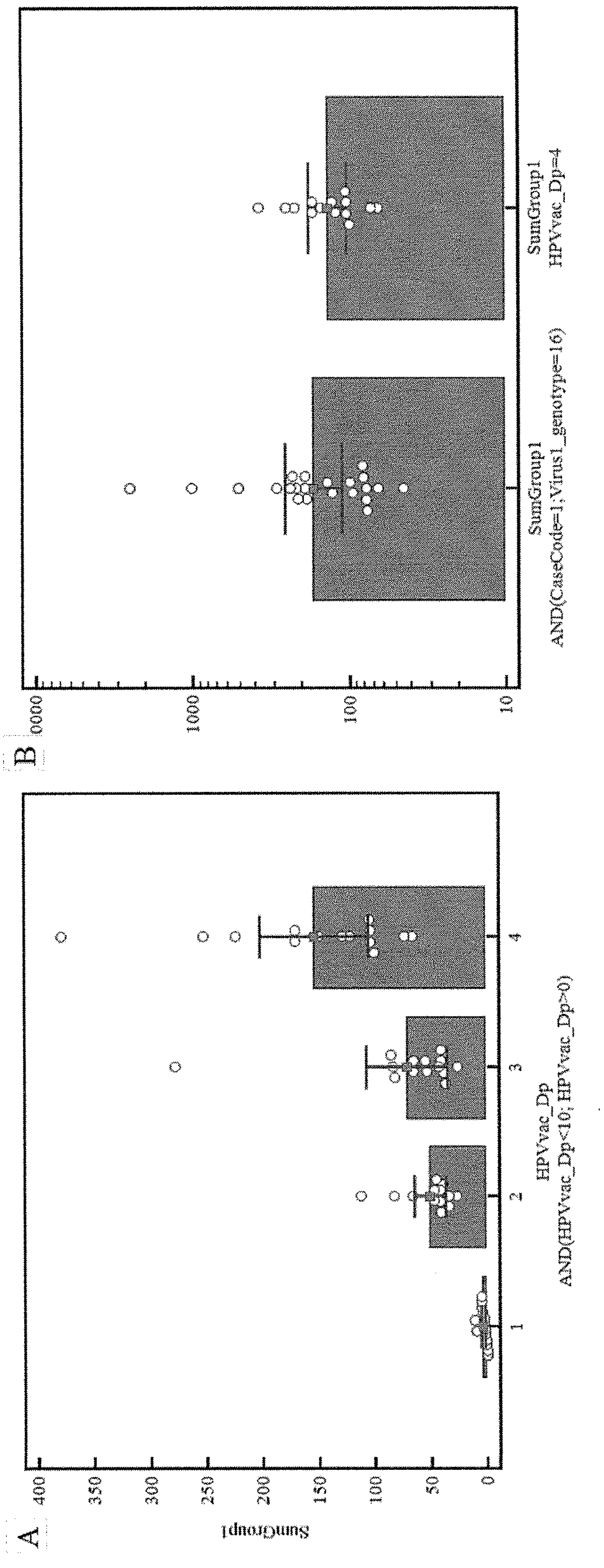
FIG. 17 Panel A depicts analysis of the total IgG reactivity to Group 1 peptides using sera from a cohort of vaccinees from 4 different vaccination time points. Panel B depicts analysis of the total IgG reactivity to Group 1 peptide antigens of HPV16 infected patients (left bar) and vaccinated individuals post-vaccination sera (right bar).
Figure 18:
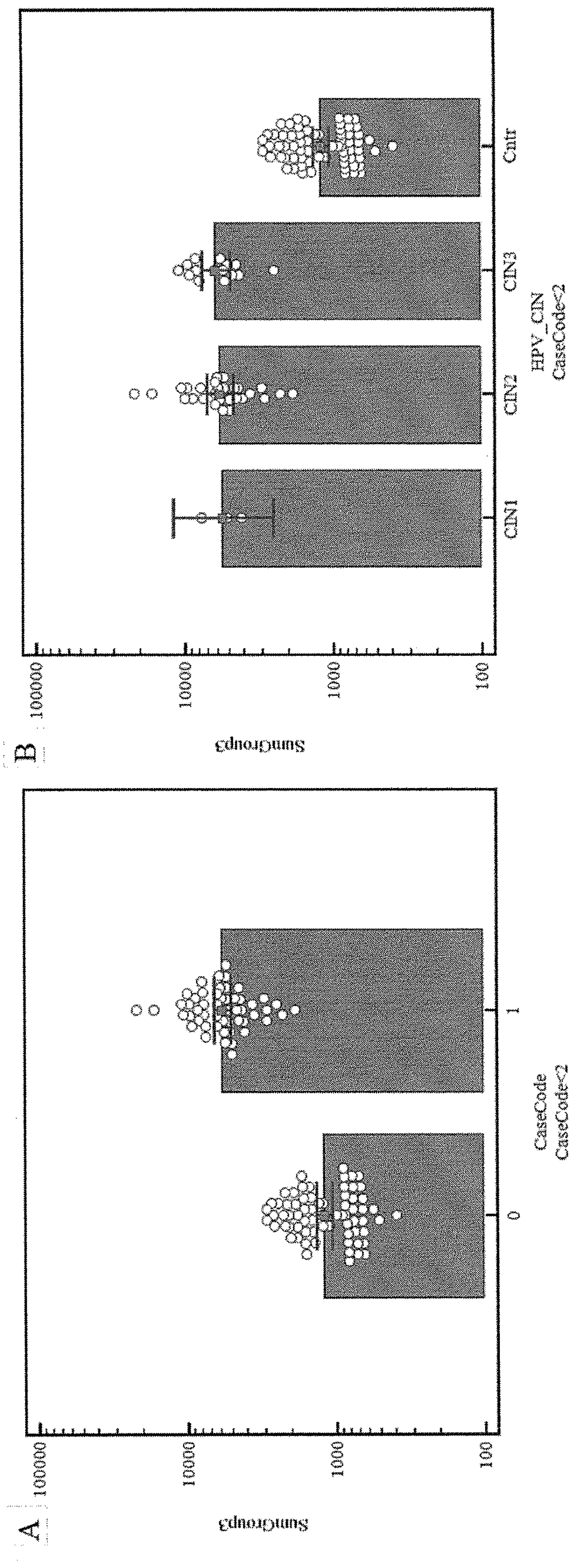
FIG. 18 depicts analysis of the total IgG reactivity to Group 3 peptide antigens of patients with diagnosed precancerous dysplasia. Panel A depicts Group 3 selected marker peptides read sum of case group (marked as 1) compared with control group (marked as 0). Panel B depicts Group 3 read sum levels of CIN1, CIN2 and CIN3 patients, Cntr indicates control samples.

Analysis yielded in 24577 peptides, 1401 of which were associated with vaccination, and the rest with cervical intraepithelial neoplasia. The most vaccination-specific peptides (Group 1, 317 peptides from 1401) with the reads count rise at least 5 times after the vaccination compared with prevaccination reads count were studied specifically. Group 1 peptides read sum values for four different vaccination time points (1-4) are shown on FIG. 16, panel A. The HPV16 infected patients sera showed also reactivity to Group 1 peptides. The total IgG reactivity to Group 1 peptides of HPV16 infected patients (FIG. 17, B, left bar) was on average slightly higher than the average read sum of post-vaccination sera of vaccinees after the last vaccination (FIG. 17, B, right bar). Average Group 3 (12700 peptides) was formed from precancerous stage-specific peptides with reads sum over case samples at least 3 times higher than sum over the control samples (FIG. 18).

Example 9

Forming an Antibody Activity Profile and Epitope Profile for Biological Sample Diagnosed with Colon Cancer Cancer is a clinically heterogeneous disease with each tumour demonstrating a distinct molecular signature. Autoantibodies produced by patients organism against aberrant changes occurring during cancer development can be detected early in a pathological process (Tomkiel et al 2002). Current invention can be used to detect any of the immunoglobulin response to the cancer antigens. In the Example 9, MVA derived motifs were identified which could potentially possess a diagnostic value in colon cancer diagnostics.

Materials and Methods

Colon cancer patients sera were processes as described in Example 1, only in part 4, step 2, 2 μl of individual serum was used instead of monoclonal antibody. Motif_Summary database constructed in Example 5 was analyzed with 2_group_comparison tool followed by analysis of motif combination tool as described in Example 6. Best combinations of the motifs that cover as many cases and as few controls were selected.

Results

Figure 19:
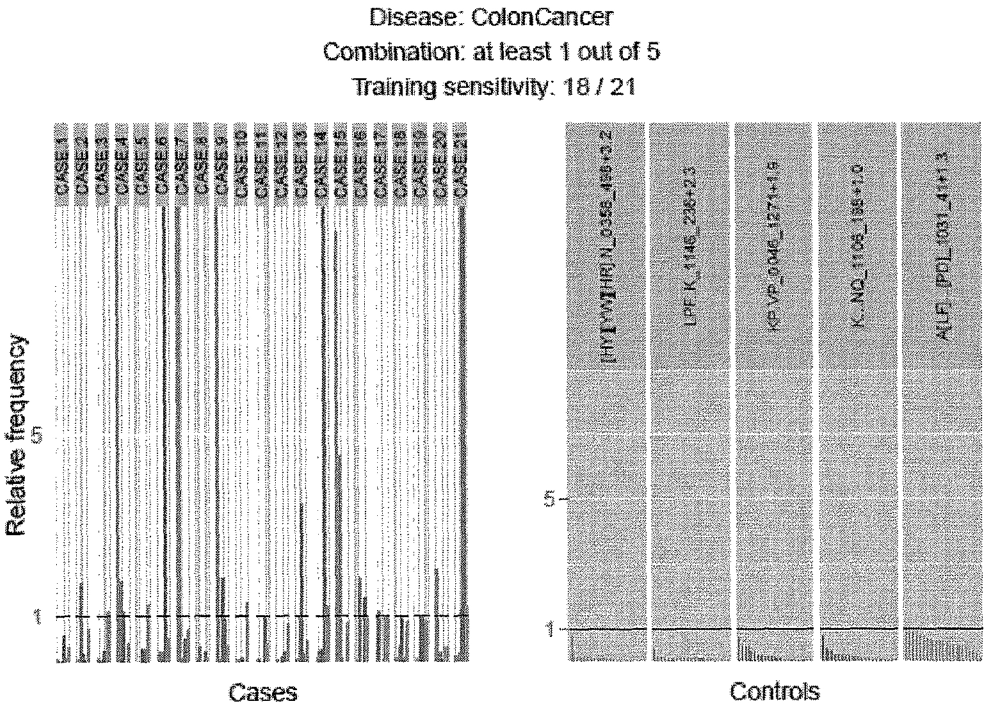
FIG. 19 depicts colon cancer specific motif panel identified by MVA covered the colon cancer samples with 86% specificity and 100% specificity.

Clinically verified colon cancer samples were analyzed as described and cluster [HY][YW][HR].N (SEQ ID NO. 43) composed of 749 unique peptides was found to be most enriched toward cases. Panel of five best motifs covered the analyzed cases with 86% specificity and 100% specificity (FIG. 19).

Example 10

Forming an Antibody Activity Profile and Epitope Profile for Biological Sample Diagnosed with Sarcoidosis Several conditions related to immune system disorders appear to be significantly associated with the onset of sarcoidosis (Subramanian et al 2004). Also, autoimmune disorders, infections with unknown pathogens or enviromental factors has been implicated as a possible cause of the disease. In the current example MVA profiling has been applied to find specific antibody activity profiles characteristic to sarcoidosis.

Materials and Methods

The sarcoidosis patients samples were processed according to the protocol presented in Example 1, except that in part 4, step 2, a respective serum sample of 2 μl was used instead of monoclonal antibody. Motif_Summary database constructed in Example 5 was analyzed with 2_group_comparison tool followed by analysis of motif combination tool as described in Example 6.

Results

Figure 20:
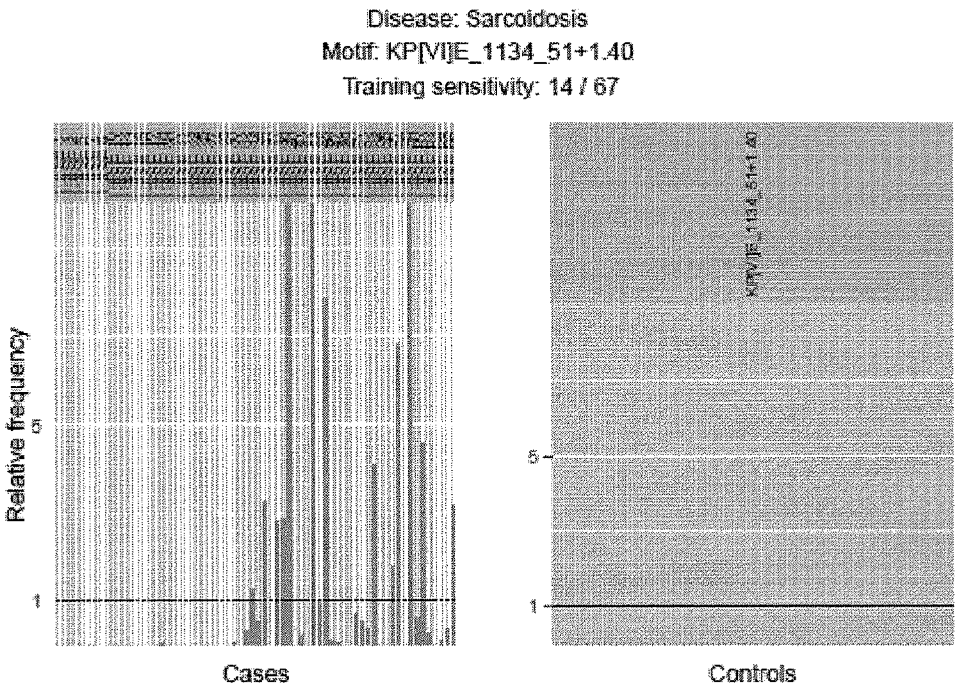
FIG. 20 depicts MVA profiling of sarcoidosis sera resulted in the discovery of the motif KP[VI]E (SEQ ID NO. 35), discriminating sarcoidosis samples with 21% sensitivity and 100% specificity.

MVA profiling of sarcoidosis sera resulted in the discovery of the motif KP[VI]E (SEQ ID NO. 35). This motif was prevalent in the sera of 14 sarcoidosis patients, no control sample showed high occurrence of this motif (FIG. 20).

Example 11

Forming an Antibody Activity Profile and Epitope Profile for Biological Sample Diagnosed with Narcolepsy Narcolepsy is a chronic neuronal disorder where person sleep-wake cycle is deregulated. In addition to the genetically determined factors, streptococcal infection or autoimmune responce against hypocretin (orexin) neurons caused by vaccination against 2009 H1N1 influenza has been implicated with onset of disease (Aran et al 2009; Nohynek et al 2012). In a current example, patients vaccinated with H1N1 Pandemrix vaccine developed narcolepsy were analysed by MVA.

Materials and Methods

Narcolepsy patient sera and control sera was received from Helsinki University (Antti Vaheri). Control sera were collected from individuals who were vaccinated with H1N1 Pandemrix vaccine and did not develop symptoms of narcolepsy. The sera were processed as in Example 1, except that 2 μl of serum for each sample instead of the monoclonal antibody was added.

Motif_Summary database constructed in example 5 was analyzed with 2_group_comparison tool followed by analysis of motif combination tool as described in Example 6. Best combinations of the motifs covering patients developing narcolepsy were selected.

Results

Figure 21:
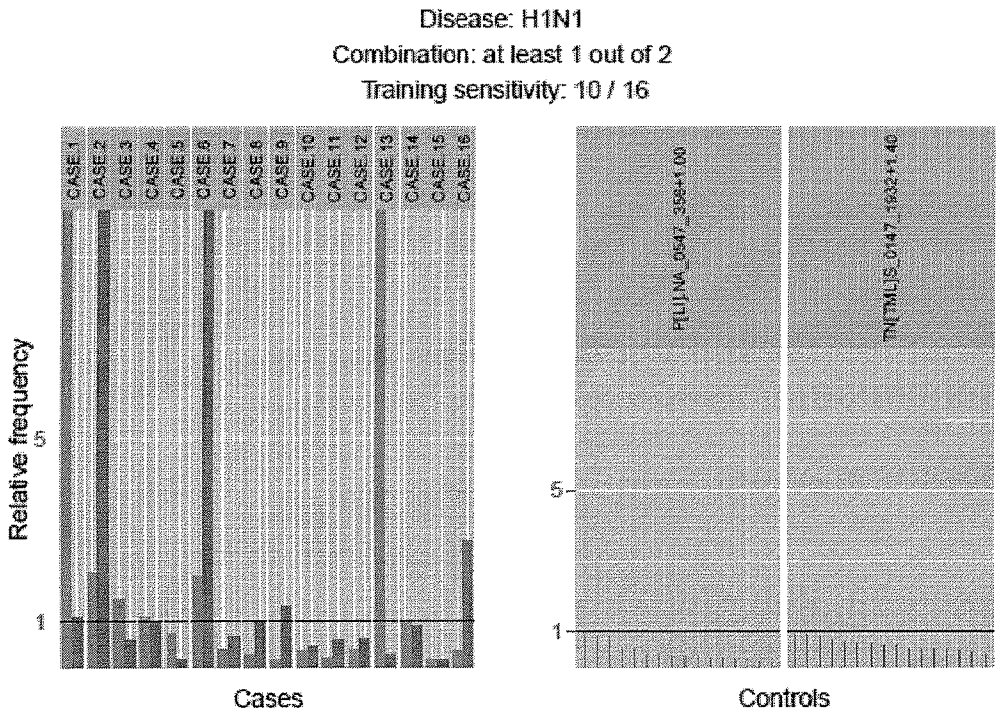
FIG. 21 depicts two motifs P[LI].NA (SEQ ID NO. 36) and TN[TML]S SEQ ID NO. 37) discriminated narcolepsy samples (Cases) from control samples with 62% specificity and 100% sensitivity.

Two motif panels P[LI].NA (SEQ ID NO. 36) and TN[TML]S (SEQ ID NO. 37) were prevalent in the samples of the patients who developed narcolepsy after Pandemrix vaccination. While no control samples showed high appearance of these two motifs, 10 patients out of 16 had either motif P[LI].NA (SEQ ID NO. 36) or motif TN[TML]S (SEQ ID NO. 37) or both aforementioned motifs presented with high frequency (FIG. 21).

Example 12

Comparison of Antibody Activity Profiles Between Individuals

Total immunoglobulin IgG levels and activity profiles are stable in serum of adult individuals with every individual having a unique activity profile. Described method for antibody activity profiling can be used to follow the IgG clonal diversity and abundance during the aging, vaccination course, infections, autoimmune diseases and other pathologic conditions. The method allows comparison of a large number of samples at most general level.

Materials and Methods

The method described in Example 1 was used for antibody profiling, with an exception in part 4, step 2, where for each individual sample 2 μl of serum was used in place of monoclonal antibody. For activity profile mapping a motif clusters database was generated (Example 5). The peptides were organized by behavior over several hundred different samples and every cluster has its specific motif, some are connected with certain pathogens or proteins (Example 6). For analysis of age dependent changes at more general level the top 500 most frequent peptides for every individual were compared pairwise to find the motif set. Motif for group of peptides is described here as a string with at least four certain amino acids at fixed positions. IgG clonal diversity was expected to be in correlation with motif count, and IgG clonal abundance was expected to be in correlation with average read sum per motif. Linear regression was used to describe the relationship between the count of motifs and age, and between average read sum per motif and age.

Results

Figure 22:
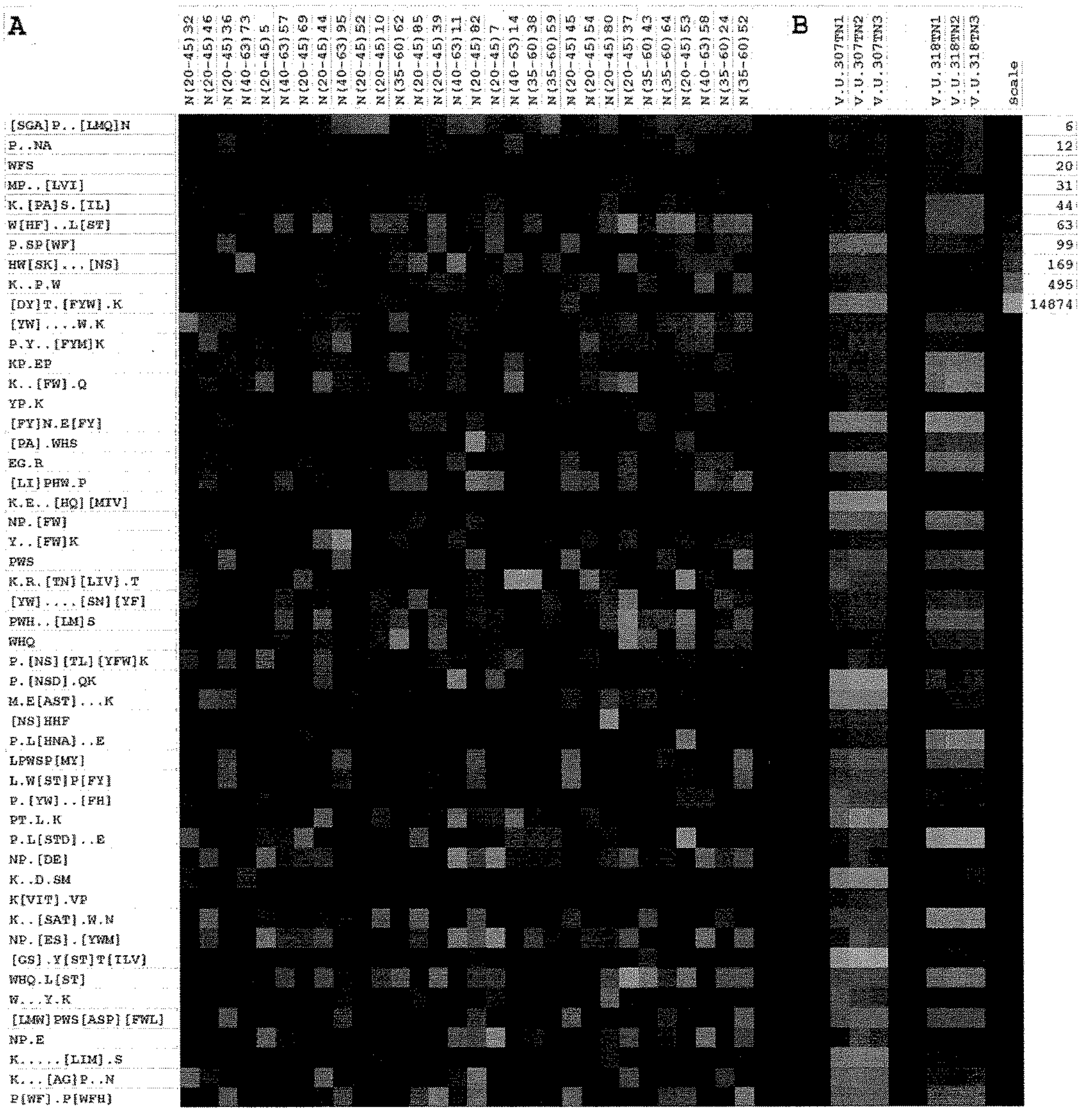
FIG. 22 depicts heat map of read sums over 50 clusters in 32 individuals. On the left side the peptide cluster defined motif is shown. On the right side of the heat map a read count scale is explained. Panel A—demonstrating the different unique IgG activity profiles of 30 donors. Panel B—IgG activity profiles of two breast cancer patients. The three samples were taken with an interval of 6 months. The heat map demonstrates the activity profile stability over one year interval.

The heat plot presented in FIG. 21 shows the profiles of different individuals over several clusters. There exist a variability of clonality among individuals (FIG. 22, A). The clonality of each individual remains stable over a course of time presenting in an individual fingerprint (FIG. 22, B).

A slight decrease of clonal diversity was seen with increasing age (significance level 0.013, FIG. 23, A). Also, there was a positive correlation between increasing age and clonal abundance (significance level<0.0001, FIG. 23, B).

Example 13

Forming an Antibody Activity Profile for Veterinary Diagnostics

The same way antibody activity profiling can reveal immunologic profiles of human pathogenic conditions, it can be used for a diagnostic purpose in livestock and domestic pets as well as laboratory animals. Different pathogens and parasites infecting cattle populations around the world are recognized as a major economic problem in the livestock industry worldwide (Reichel et al 2013). Zoonoses such as influenza virus and rotavirus, affecting wild and domestic animals can also be transferred to humans (Karesh et al 2012). The global occurrence and re-occurrence of transboundary diseases like foot-and-mouth disease, classical swine fever or bovine viral diarrhoea virus indicates that there is a high need for the development of powerful, robust and high-capacity biomarkers. In Example 13 the essence of the MVA profiling is shown also to apply to non-human samples.

Materials and Methods

Bovine sera samples were obtained from (Estonian University of life Sciences). Samples were prepared as described in Example 1, except in part 4, step 2 for each individual sample 2 μl of respective serum was added instead of the monoclonal antibody. Hundred most frequently observed peptides from 50 randomly selected human samples and same number highest count peptides from 50 bovine sera were presented as heat map.

Results

Figure 24:
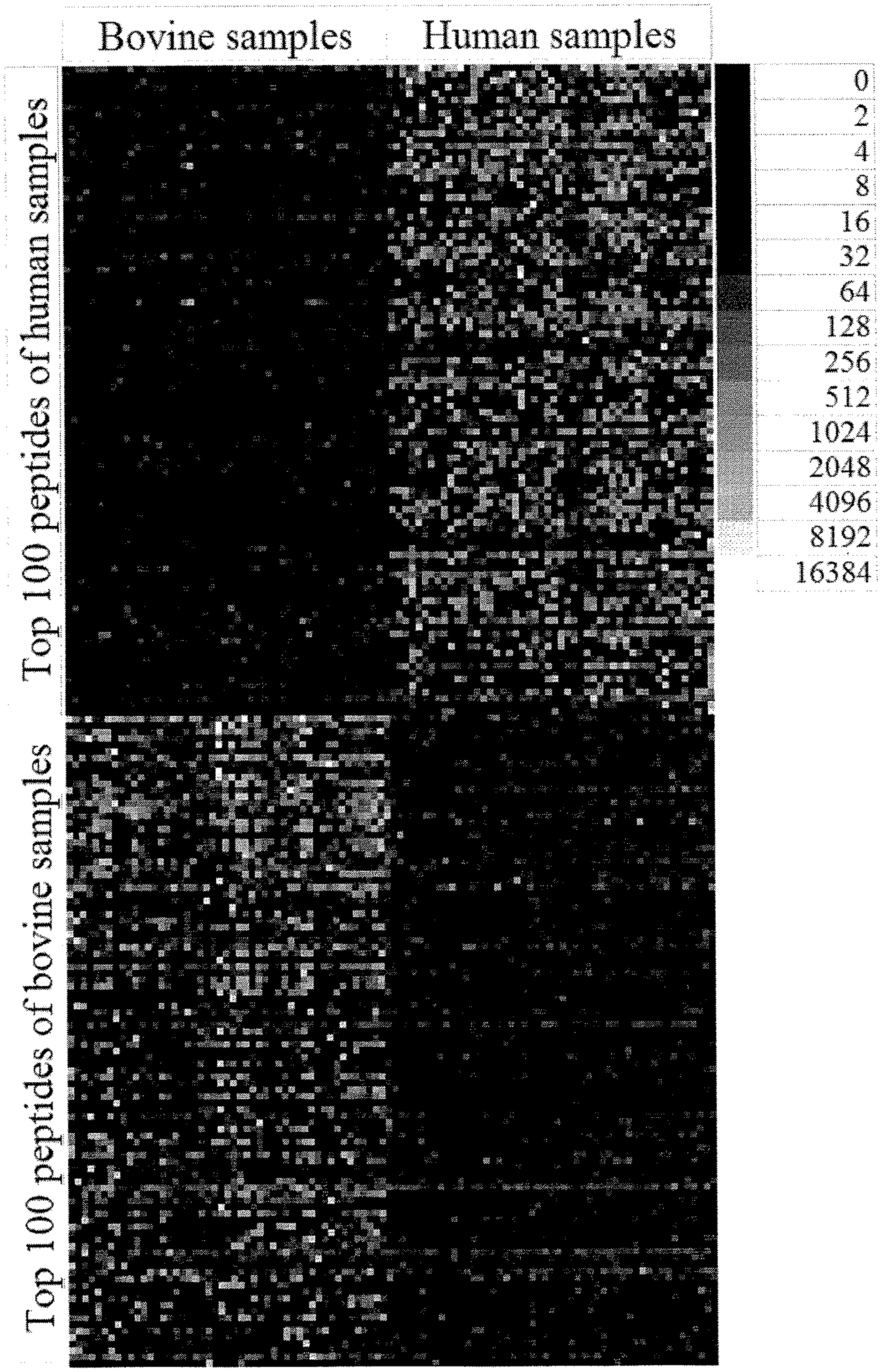
FIG. 24 depicts heat map of the bovine and human specific high frequency peptides. Observed antibody activity profiles indicate completely different epitope pattern directed against species-specific pathogens.

The results show that using the method described in Example 1 it is also possible to identify non-human immunoglobulin profiles. Additionally, the data indicate that antibody activity profiles obtained from bovine or human samples do not overlap (FIG. 24). Since the most frequent peptides were showing nonrandom intraspecies distribution it was concluded that pattern reflects the species-specific immune epitope profiles specific to non-overlapping set of pathogens.

REFERENCES

Karesh W B, Dobson A, Lloyd-Smith J O, Lubroth J, Dixon M A, Bennett M, Aldrich S, Harrington T, Formenty P, Loh E H, Machalaba C C, Thomas M J, Heymann D L (2012) Ecology of zoonoses: natural and unnatural histories. Lancet. 380(9857):1936-45.

Reichel M P, Alejandra Ayanegui-Alcerreca M, Gondim L F, Ellis J T. What is the global economic impact of *Neospora caninum* in cattle—the billion dollar question (2013) Int J Parasitol. 43 (2):133-42.

Example 14

Profiling Antibodies Other than Immunoglobulin G

Serum antibody fraction contains different antibody classes. With the method described herein profiles of different types of antibodies, can be detected. In the example below IgE profiling is described, however by changing the immunoglobulin binding monoclonal antibody affinity, different subsets of immunoglobulins (IgG, IgA, IgD, IgM, IgE) can be detected in the body fluids using the protocol described in Example 14 followed by Example 1, part 6 to the end. Immunoglobulin E is often heightened in the serum of allergic individuals. However IgE can sometimes also be detected in the serum of individuals with helminthic invasion.

For allergenic component mapping, peptide antigen panel is shown to be suitable. Allergen epitope mimicking peptides have been shown to perform well in several allergen detection arrays (Chatchatee et al 2001; Busse et al 2002; Beyer et al 2005; Untersmayr et al 2006; Matsumoto et al 2009; Lin et al 2009; Ruppel et al 2010; Vereda et al 2010). Furthermore, allergen epitope mimicking peptides have been shown to raise the specificity and prognostic value of the diagnostic testing of allergy (Shreffler et al 2004; Matsuo et al 2005; Battais et al 2005; Beyer et al 2005; Matsumoto et al 2009).

The method described here could allow further composition of peptide arrays with fixed, already known mimotopes as well as screening and subsequent characterization of the unknown allergen IgE profiles. Short mimotopes related to the allergen epitopes also allow simultaneous allergen determination from the single serum sample with relatively low cost.

Materials

The serum of allergy patients and non-allergic controls were obtained from Tartu University Hospital, Estonia. All allergy patients were clinically confirmed to have a very high reactivity towards dust mite extract or allergen mix containing dust mite extract, cockroach extract and a house-dust. Non-allergic controls were verified not to be allergic to dust mix.

Methods

Part 1. Preparation of the Magnetic Beads

In order to capture IgE from serum, mouse monoclonal antihuman IgE antibodies (clone B3102E8, Antibodies-online, GA, USA) were immobilized on tosylactivated magnetic beads (#14203, Invitrogen) following the manufacturers protocol. However any other anti-immunoglobulin antibody can be attached to the activated surface of magnetic beads.

Anti-IgE Antibody Coupled Magnetic Beads were then Incubated with Serum:

1. 150 μl of 1:1,5 diluted serum sample in buffer (lx PBS, 0.1% Tween 20, 0.1% BSA) was mixed with 0.9 mg of conjugated beads.
2. The sample was incubated with tilting and rotation ON at 4° C. to capture the target protein (IgE in a current protocol).
3. Unbound antibodies and serum components were removed by washing beads several times with 1×PBS—0.05% Tween 20. Beads were dissolved in PBS—0.05% Tween 20 with final concentration of 20 mg/ml.

Part 2. Library Preclearing

Prior biopanning, phage library preclearing was performed to remove beads and anti-IgE binding antibodies.

1. 10.5 μl of 1×PBS—0.5% BSA buffer per sample was placed into a new Protein Lobind tube (#022431064, Eppendorf) and mixed.
2. Subsequently 2.5 μl ($2.5\times10^{10}$ particles) or 5 μl ($5\times10^{10}$ particles) of naïve Ph.D.™-12 Phage Display Peptide library (#E8111L, NEB) per individual sample was added.
3. This was followed by addition of 25 μg of anti-IgE monoclone conjugated beads per individual sample. The sample was then incubated rotating for 1 h at RT.
4. After incubation, the sample was spinned briefly, placed onto the magnet and the supernatant containing precleared library was transferred into another tube and used in biopanning.

Part 3. Affinity Selection of Phages

Magnetic bead immobilized serum IgE complexes were incubated with precleared phage library to select IgE paratope binding phages.

1. 240 μl of PBS—0.05% Tween 20 was added to a new tube.
2. Then, 14 μl of precleared library (adjusted according to the input $2.5\times10^{10}$ or $5\times10^{10}$ particle of naïve 12mer library) was added.
3. This was followed by addition of 45 μl of immobilized IgE—bead complex, obtaining bead concentration of 3 mg/ml.
4. Sample was then incubated for 2.5 h at 4° C.
5. After that the tube was centrifuged at 1000 g for 1 min and magnetic field was applied for 5 min, followed by removal of supernatant.
6. The sample was subjected to three subsequent washed with 1 ml of PBS—Tween 0.5% and finally the beads were gently resuspended in 100 μl of 1×PBS.

7. The protocol was continued as described in Example 1, starting from part 6 to the end.
8. The sequences obtained from HTS were analyzed as described in example 1. This was followed by data analysis with 2_sample_comparison tool as described in example 2.
9. BLAST alignment (http://blast.ncbi.nlm.nih.gov/Blast.cgi) was performed on top peptides.

Results

Figure 25:
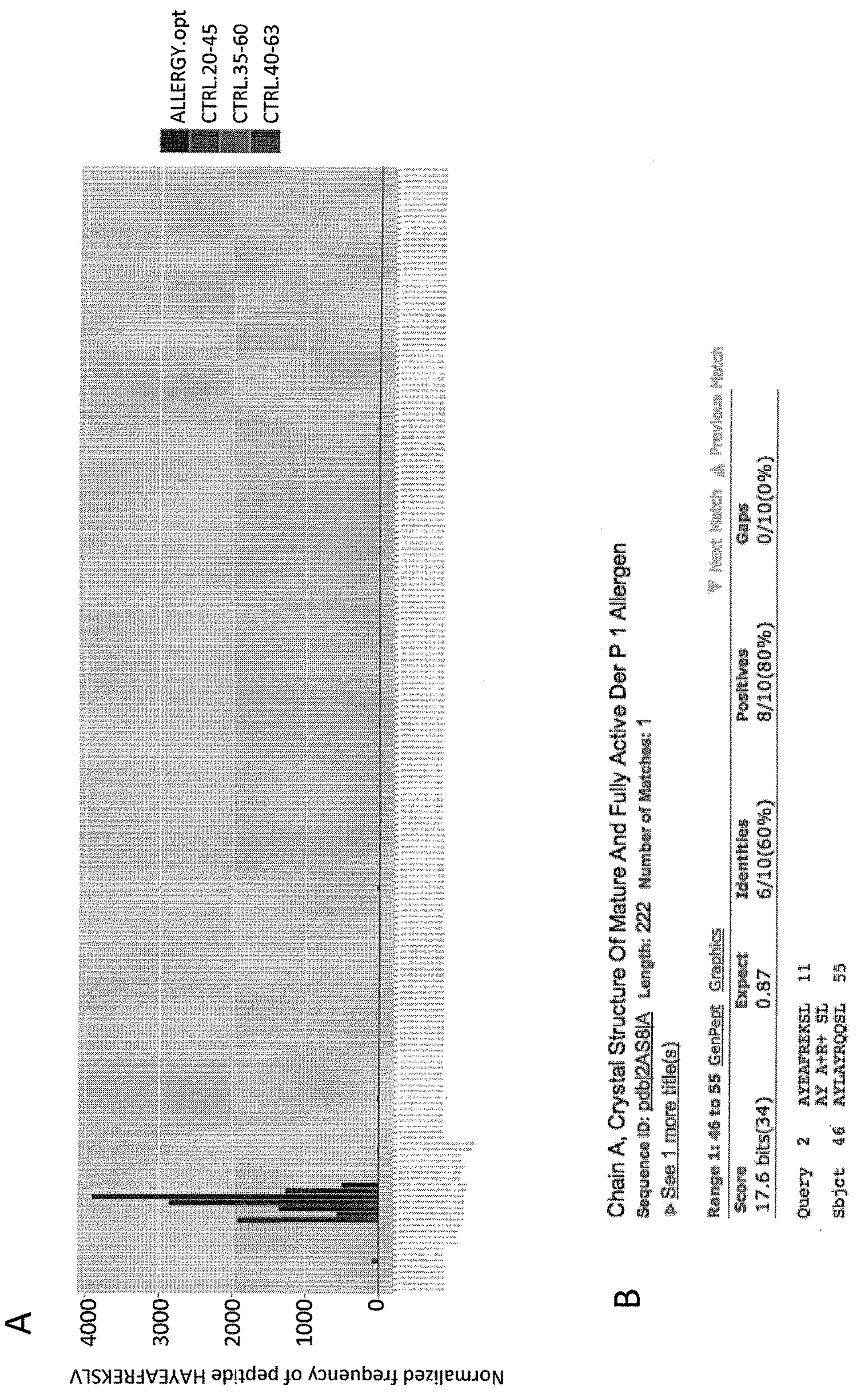
FIG. 25 depicts identification of peptide HAYEAFREKSLV (SEQ ID NO. 38) as a dust mite specific sequence. Panel A—HAYEAFREKSLV (SEQ ID NO. 38) peptide expression in dust mite allergic patient. Shown is the analysis of the frequency of occurrence (counts) of the peptide in the sera of individual diagnosed with dust mite allergy in comparison with controls. Seven subsequent samples showing high count number of HAYEAFREKSLV (SEQ ID NO. 38) are parallels of the same sera sample. Panel B—The alignment of the peptide on Der p1 using BLAST.

The results identified peptide HAYEAFREKSLV (SEQ ID NO. 38) as one of the top two peptides with the highest count in allergic samples (FIG. 25, A). BLAST analysis mapped the aforementioned peptide on dust mite (*Dermatophagoides* spp) major allergen Der p1 (and Der f1, data not shown) protein (PDB 2AS8_A)(FIG. 25, B). This cystein protease represents one of the most prevalent dust mite allergenic proteins along with Der p2.

Figure 26:
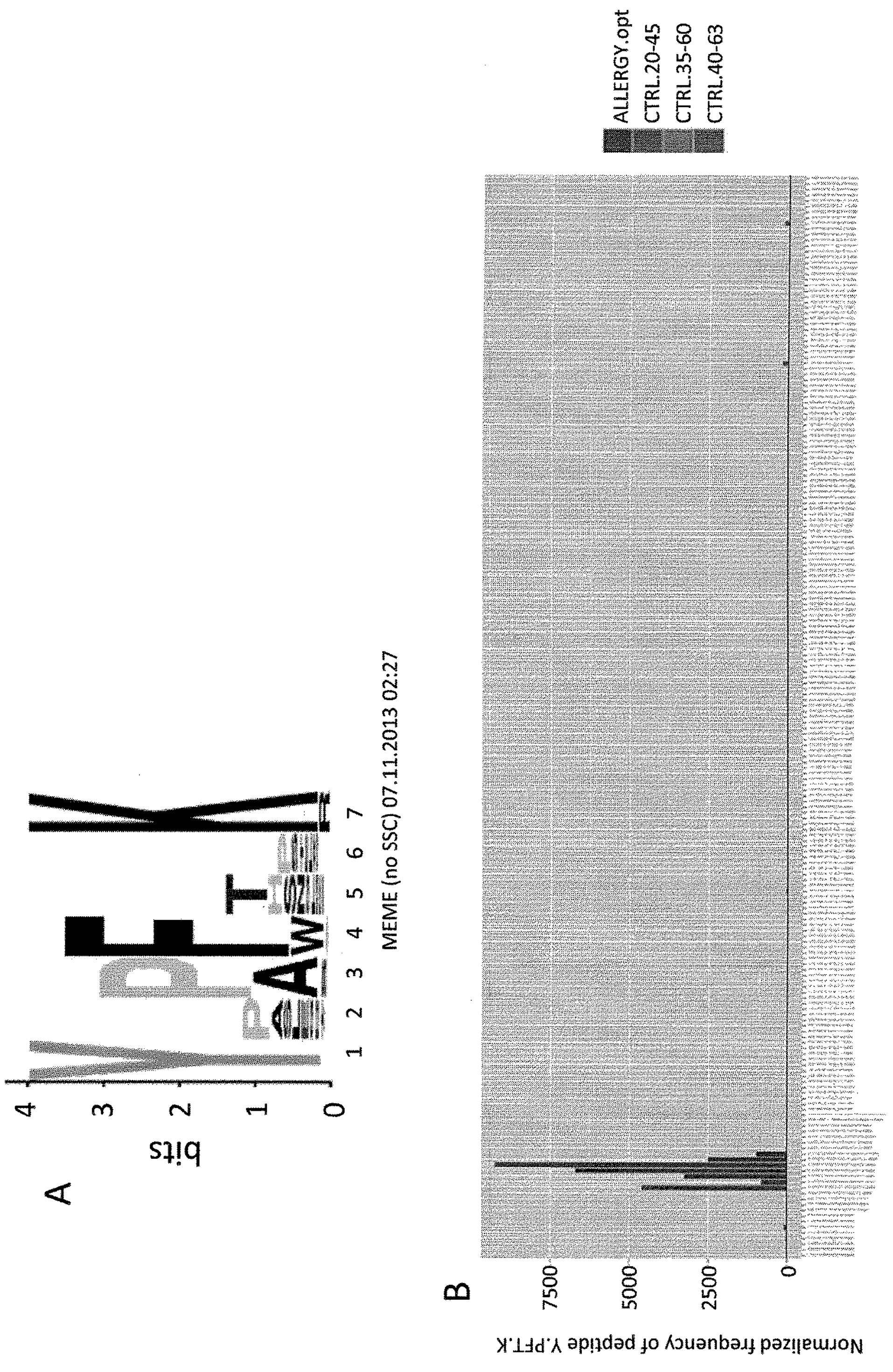
FIG. 26 depicts identification of the top motif Y.PFT.K (SEQ ID NO. 39) as allergy sample specific. Panel A—MEME analysis of a set of peptides identified as dust-mite allergy specific revealed a top motif that was present in 133 peptides out of top 1000. Panel B—Shown is the analysis of the frequency of occurrence (counts) of the motif Y.PFT.K (SEQ ID NO. 39) in the sera of individual diagnosed with dust mite allergy in comparison with controls. Seven subsequent samples showing high presence of motif Y.PFT.K (SEQ ID NO. 39) are parallels of the same sera sample.

The bioinformatical processing of 1000 top peptides from sera of the individual diagnosed with dust mite allergy, identified a motif with the sequence Y.[PA]FT.K (SEQ ID NO. 44) (FIG. 26, A) that was present in 133 unique peptides and discriminated this individual form control samples (FIG. 26, B).

Additionally to the feasibility of IgE mimotope profiling, the results presented here reveal the ability to detect sample specific motifs from the sample parallels, confirming the consistency of the described method.

REFERENCES

Berzofsky J A, Berkower I J (1993) Immunogenicity and antigen structures. In Fundamental Immunology (Ed. Paul, W.), Raven Press:235-282.

Buus S, Rockberg J, Forsstrom B, Nilsson P, Uhlen M, Schafer-Nielsen C (2012) High-resolution mapping of linear antibody epitopes using ultrahigh-density peptide microarrays. Mol Cell Proteomics. 11(12):1790-800.

Paul, W. E (1993) The Immune System: an Introduction. In Fundamental Immunology (Ed. Paul, W.), Raven Press: 1-21.

Suber T L, Casciola-Rosen L, Rosen A (2008) Mechanisms of disease: autoantigens as clues to the pathogenesis of myositis. Nat Clin Pract Rheumatol. 4(4):201-9.

Battais F, Mothes T, Moneret-Vautrin D A, Pineau F, Kanny G et al (2005) Identification of IgE-binding epitopes on gliadins for patients with food allergy to wheat. Allergy. 60:815-821.

Beyer K, Jarvinen K M, Bardina L, Mishoe M, Turjanmaa K et al (2005) IgE-binding peptides coupled to a commercial matrix as a diagnostic instrument for persistent cow's milk allergy. *J Allergy Clin Immunol.* 116: 704-705.

Busse P J, Järvinen K M, Vila L, Beyer K, Sampson H A (2002) Identification of sequential IgE-binding epitopes on bovine alpha(s2)-casein in cow's milk allergic patients. *Int. Arch. Allergy Immunol.* 129:93-96.

Chatchatee P, Jarvinen K M, Bardina L, Beyer K, Sampson H A (2001) Identification of IgE- and IgG-binding epitopes on alpha(s1)-casein: differences in patients with persistent and transient cow's milk allergy. *J Allergy Clin Immunol.* 107(2):379-83.

Lin J, Bardina L, Shreffler W G, Andreae D A, Ge Y et al (2009) Development of a novel peptide microarray for large-scale epitope mapping of food allergens. *J Allergy Clin Immunol.* 124(2):315-22.

Matsuo H, Kohno K, Niihara H, Morita E (2005) Specific IgE determination to epitope peptides of omega-5 gliadin and high molecular weight glutenin subunit is a useful tool for diagnosis of wheat-dependent exercise-induced anaphylaxis. *J Immunol,* 175: 8116-8122.

Matsumoto N, Okochi M, Matsushima M, Kato R, Takase T et al (2009) Peptide array-based analysis of the specific IgE and IgG4 in cow's milk allergens and its use in allergy evaluation. *Peptides.* 30(10): 1840-7.

Ruppel E, Aŷ B, Boisguerin P, Done S, Worm M et al (2010) Identification of IgE binding to Apí ǵ 1-derived peptides. *Chembiochem.* 11(16):2283-93.

Shreffler W G, Beyer K, Chu T H, Burks A W, Sampson H A (2004) Microarray immunoassay: association of clinical history, in vitro IgE function, and heterogeneity of allergenic peanut epitopes. *J Allergy Clin Immunol.* 113 (4): 776-82.

Vereda A, Andreae D A, Lin J, Shreffler W G, Ibañez M D et al (2010) Identification of IgE sequential epitopes of lentil (Len c 1) by means of peptide microarray immunoassay. *J Allergy Clin Immunol.* 126(3):596-601.el.

Untersmayr E, Szalai K, Riemer A B, Hemmer W, Swoboda I et al (2006) Mimotopes identify conformational epitopes on parvalbumin, the major fish allergen. *Mol Immunol.* 43(9):1454-61.

What is claimed is:

1. A method of forming a metadatabase of minimal epitope profiles for use in a diagnostic, the method comprising:

a) providing a plurality of biological samples;

b) performing antibody activity profiling of an immunoglobulin fraction of the samples to form a data set of peptide profiles for each sample, wherein the peptide profiles comprise antigen-antibody interaction sequences, wherein the antibody activity profiling comprises the steps of:
- i) pre-clearing a random phage display library of peptides to reduce nonspecific binding to immunoglobulins, wherein the peptides within the library are a same length,
- ii) preabsorbing an immunoglobulin fraction of the samples with a mutated control phage,
- iii) affinity binding the library of peptides to the preabsorbed immunoglobulin fraction of the samples,
- iv) generating complementary DNA (cDNA) encoding the affinity bound peptides with primer sets that select for amplicons encoding peptides from the library over amplicons from the mutated control phage, further wherein the amplicons encoding peptides from the library and the amplicons from the mutated phage comprise 5' and 3' amplification adapters with same phenotypes,
- v) sequencing the cDNA, and
- vi) selecting for cDNA sequences encoding peptides from the library by length to form the data set of peptide profiles;

c) comparing peptide profiles across different samples to generate a meta-profile defined by an amino acid sequence of the motif and its frequency pattern;

d) assigning a diagnosis or disorder to differentially expressed meta-profiles generated from samples affected by the diagnosis or disorder;

e) constructing a meta-database containing minimal epitope clusters (motif_summary), defined according to the peptide frequency patterns over multiple samples;

f) constructing a database of peptide frequencies (pep_summary), where frequency of occurrence of each of the peptide antigen is recorded for all samples;

g) aligning peptides of a characterized sample to reveal similarity in amino acid sequence thereby defining the sequence of the minimal epitope;

h) verifying the minimal epitope by harboring a connected identifier—proteinaceous antigen compound wherein the identifier is a molecule or substance allowing later identification of the respective peptide identity;

i) providing an enriched affinity sample for minimal epitope defining sequence generation;

j) providing a source data for metadatabase and any database underlying it by any amplification and sequence identification method; and k) generating a peptide comprising the minimal epitope as a diagnostic for the diagnosis or disorder.

2. The method according to claim 1, wherein the identifier is a nucleic acid.

3. The method according to claim 1, wherein the library is encoded in a plurality of amplicons, each amplicon comprising a DNA region encoding a different random peptide flanked by adaptor regions and a unique bar code sequence.

4. The method according to claim 3, wherein:

a) the step of pre-clearing the random phage display library of peptides comprises exposing the library of peptides to a preclearing agent selected from the group consisting of an immobilized or a soluble compound, a surface material, plastic, and a competitive antigen;

b) the step of affinity binding the library of peptides comprises mixing the pre-absorbed immunoglobulins (Ig) fraction, a mounted capture reagent and the precleared library of peptides under conditions that permit specific binding between the peptides with and capture of the immunoglobulins with the capture reagent;

c) between steps iii) and iv) the method comprises collecting, and isolating the peptide library containing amplicon for amplification; and d) after the step of selecting for cDNA sequences, the method comprises normalizing the amplified amplicons so that each barcode within a 3' primer of the primer set is about equal.

5. The method according to claim 1, wherein the immunoglobulin fraction comprises a monoclonal antibody fraction thereby establishing an epitope recognition pattern for the monoclonal antibody from the library of peptides.

6. The method according to claim 1, wherein the immunoglobulin fraction is a polyclonal antibody fraction.

7. The method according to claim 1, wherein the biological samples are collected from a population of humans thereby forming a peptide profile group of the population.

8. The method according to claim 1, wherein the biological samples a group of individuals grouped according to a group characteristic for generating a peptide profile for comparison to a peptide profile group.

9. The method of claim 1 wherein the method of providing source data for metadatabase is PCR amplification of DNA amplicon and DNA sequencing and subsequently aligning the sequenced amplicon regions to form a consensus sequence.

10. The method of claim 1, wherein the minimal epitope defining sequence are two to twelve amino acids in length.

11. The method according to claim 1, wherein the difference in peptide profile is assigned to a single individual or a group of individuals.

12. The method according to claim 11, wherein the individual or group of individuals are suffering from a medical condition.

13. The method according to claim 1, wherein the biological sample is sera or plasma.

14. The method of claim 1, wherein the immunoglobulin fraction is preabsorbed with a control sample comprising sera.

15. The method of claim 4, wherein the capture reagent is protein A or protein G or protein L of mixture capture reagents and the solid support is a magnetic bead or nonmagnetic bead.

16. The method of claim 1, wherein the primer sets target specific adaptor regions and unique bar codes.

17. The method according to claim 16, wherein the unique bar code sequence comprises 4 nucleic acid bases of different order than those in other amplicons, each nucleic acid base selected from the group consisting of guanine (G), adenine (A), thymine (T) and cytosine (C).

18. The method according to claim 16, wherein the unique bar code sequence comprises 6 nucleic acid bases of different order than those in other amplicons, each nucleic acid base selected from the group consisting of guanine (G), adenine (A), thymine (T) and cytosine (C).

19. A method of forming a vaccination peptide profile, the method comprising:

a) performing the method of claim 4 with samples from a time point before a vaccination and a time point after a vaccination to form a peptide profile for each time point; and b) comparing the peptide profiles between time points to establish a peptide profile indicative of vaccination.

* * * * *

SEQUENCE LISTING

```
<160> NUMBER OF SEQ ID NOS: 44

<210> SEQ ID NO 1
<211> LENGTH: 242
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: n is a, c, g, or t
<220> FEATURE:
<221> NAME/KEY: misc_feature
<222> LOCATION: (1)..(242)
<223> OTHER INFORMATION: n is a, c, g, or t

<400> SEQUENCE: 1

aatgatacgg cgaccaccga gatctacact gatctagtgg tacctttcta ttctcactct      60

nnknnknnkn nknnknnknn knnknnknnk nnknnkggtg gaggttcggc cgaaactgtt     120
```

gaaagttgtt tagcaaaatc ccatacagaa aattcattta ctaacgtctg gaaagacgac 180
aaaactttag atcgttacgc taactatgag ggnnnnnnat ctcgtatgcc gtcttctgct 240
tg 242

<210> SEQ ID NO 2
<211> LENGTH: 25
<212> TYPE: DNA
<213> ORGANISM: Artificial Sequence
<220> FEATURE:
<223> OTHER INFORMATION: sythetic construct

<400> SEQUENCE: 2
tagtggtacc tttctattct cactc 25

<210> SEQ ID NO 3
<211> LENGTH: 19
<212> TYPE: DNA
<213> ORGANISM: Artificial Sequence
<220> FEATURE:
<223> OTHER INFORMATION: synthetic construct

<400> SEQUENCE: 3
gttacgctaa ctatgaggg 19

<210> SEQ ID NO 4
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(6)
<223> OTHER INFORMATION: Xaa can be any naturally occuring amino acid

<400> SEQUENCE: 4

Asp Tyr Lys Xaa Xaa Asp
1 5

<210> SEQ ID NO 5
<211> LENGTH: 7
<212> TYPE: PRT
<213> ORGANISM: Artificial Sequence
<220> FEATURE:
<223> OTHER INFORMATION: synthetic sequence
<220> FEATURE:
<221> NAME/KEY: MISC_FEATURE
<222> LOCATION: (1)..(7)
<223> OTHER INFORMATION: Xaa can be any naturally occurring amino acid

<400> SEQUENCE: 5

Tyr Xaa Xaa Thr Leu Xaa Tyr
1 5

<210> SEQ ID NO 6
<211> LENGTH: 36
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(36)
<223> OTHER INFORMATION: n is a, c, g, or t

<400> SEQUENCE: 6
nnknnknnkn nknnknnknn knnknnknnk nnknnk 36

<210> SEQ ID NO 7
<211> LENGTH: 34
<212> TYPE: DNA
<213> ORGANISM: Artificial Sequence
<220> FEATURE:
<223> OTHER INFORMATION: synthetic construct

<400> SEQUENCE: 7
aatgatacgg cgaccaccga gatctacact gatc 34

<210> SEQ ID NO 8
<211> LENGTH: 30
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(30)
<223> OTHER INFORMATION: n is a, c, g, or t

<400> SEQUENCE: 8
nnnnnnatct cgtatgccgt cttctgcttg 30

<210> SEQ ID NO 9
<211> LENGTH: 194
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(194)
<223> OTHER INFORMATION: n is a, c, g, or t

<400> SEQUENCE: 9
aatgatacgg cgaccaccga gatctacact gatctagtgg taccgtttta ctcccactct 60
gccgaaactg ttgaaagttg tttagcaaaa tcccatacag aaaattcatt tactaacgtc 120
tggaaagacg acaaaacttt agatcgttac gctaactatg agggnnnnnn atctcgtatg 180
ccgtcttctg cttg 194

<210> SEQ ID NO 10
<211> LENGTH: 60
<212> TYPE: DNA
<213> ORGANISM: Artificial Sequence
<220> FEATURE:
<223> OTHER INFORMATION: synthetic construct

<400> SEQUENCE: 10
aatgatacgg cgaccaccga gatctacact gatctagtgg taccgtttta ctcccactct 60

<210> SEQ ID NO 11
<211> LENGTH: 26
<212> TYPE: DNA
<213> ORGANISM: Artificial Sequence
<220> FEATURE:
<223> OTHER INFORMATION: synthetic construct

<400> SEQUENCE: 11
tagtggtacc gttttactcc cactct 26

<210> SEQ ID NO 12
<211> LENGTH: 20

-continued

<212> TYPE: DNA
<213> ORGANISM: Artificial Sequence
<220> FEATURE:
<223> OTHER INFORMATION: synthetic construct

<400> SEQUENCE: 12
cgttacgcta actatgaggg 20

<210> SEQ ID NO 13
<211> LENGTH: 20
<212> TYPE: DNA
<213> ORGANISM: Artificial Sequence
<220> FEATURE:
<223> OTHER INFORMATION: synthetic construct

<400> SEQUENCE: 13
tgtactttgt ttcgcgcttg 20

<210> SEQ ID NO 14
<211> LENGTH: 20
<212> TYPE: DNA
<213> ORGANISM: Artificial Sequence
<220> FEATURE:
<223> OTHER INFORMATION: synthetic construct

<400> SEQUENCE: 14
aacggctaca gaggctttga 20

<210> SEQ ID NO 15
<211> LENGTH: 60
<212> TYPE: DNA
<213> ORGANISM: Artificial Sequence
<220> FEATURE:
<223> OTHER INFORMATION: synthetic construct

<400> SEQUENCE: 15
aatgatacgg cgaccaccga gatctacact gatctagtgg tacctttcta ttctcactct 60

<210> SEQ ID NO 16
<211> LENGTH: 50
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(50)
<223> OTHER INFORMATION: n is a, c, g, or t

<400> SEQUENCE: 16
caagcagaag acggcatacg agatnnnnnn ccctcatagt tagcgtaacg 50

<210> SEQ ID NO 17
<211> LENGTH: 43
<212> TYPE: DNA
<213> ORGANISM: Artificial Sequence
<220> FEATURE:
<223> OTHER INFORMATION: synthetic construct

<400> SEQUENCE: 17
cgagatctac actgatctag tggtaccttt ctattctcac tct 43

<210> SEQ ID NO 18
<211> LENGTH: 43
<212> TYPE: DNA
<213> ORGANISM: Artificial Sequence
<220> FEATURE:

<223> OTHER INFORMATION: synthetic construct

<400> SEQUENCE: 18
ggaaagacga caaaacttta gatcgttacg ctaactatga ggg 43

<210> SEQ ID NO 19
<211> LENGTH: 8
<212> TYPE: PRT
<213> ORGANISM: Artificial Sequence
<220> FEATURE:
<223> OTHER INFORMATION: synthetic construct

<400> SEQUENCE: 19

Asp Tyr Lys Asp Asp Asp Asp Lys
1 5

<210> SEQ ID NO 20
<211> LENGTH: 10
<212> TYPE: PRT
<213> ORGANISM: Artificial Sequence
<220> FEATURE:
<223> OTHER INFORMATION: synthetic construct

<400> SEQUENCE: 20

Glu Gln Lys Leu Ile Ser Glu Glu Asp Leu
1 5 10

<210> SEQ ID NO 21
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(8)
<223> OTHER INFORMATION: I is I or L or V
Xaa can be any naturally occurring amino acid
<220> FEATURE:
<221> NAME/KEY: MISC_FEATURE
<222> LOCATION: (2)..(2)
<223> OTHER INFORMATION: I is I or L or V
<220> FEATURE:
<221> NAME/KEY: MISC_FEATURE
<222> LOCATION: (2)..(2)
<223> OTHER INFORMATION: I is I or L or V
Xaa can be any naturally occurring amino acid
<220> FEATURE:
<221> NAME/KEY: MISC_FEATURE
<222> LOCATION: (3)..(3)
<223> OTHER INFORMATION: S is S or A or G or P
<220> FEATURE:
<221> NAME/KEY: MISC_FEATURE
<222> LOCATION: (4)..(4)
<223> OTHER INFORMATION: E is E or F or M or Q
<220> FEATURE:
<221> NAME/KEY: MISC_FEATURE
<222> LOCATION: (7)..(7)
<223> OTHER INFORMATION: L is L or V

<400> SEQUENCE: 21

Leu Ile Ser Glu Xaa Xaa Leu Val
1 5

<210> SEQ ID NO 22
<211> LENGTH: 5
<212> TYPE: PRT
<213> ORGANISM: Artificial Sequence
<220> FEATURE:
<223> OTHER INFORMATION: synthetic construct
<220> FEATURE:

-continued

<221> NAME/KEY: MISC_FEATURE
<222> LOCATION: (5)..(5)
<223> OTHER INFORMATION: L is L or M

<400> SEQUENCE: 22

Leu Ile Ser Glu Leu
1 5

<210> SEQ ID NO 23
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (3)..(3)
<223> OTHER INFORMATION: Q is Q or M

<400> SEQUENCE: 23

Ala Pro Gln Pro Gly Leu Ala
1 5

<210> SEQ ID NO 24
<211> LENGTH: 5
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (2)..(2)
<223> OTHER INFORMATION: A is A or V
<220> FEATURE:
<221> NAME/KEY: MISC_FEATURE
<222> LOCATION: (3)..(3)
<223> OTHER INFORMATION: N is N or S

<400> SEQUENCE: 24

Leu Ala Asn Pro Asp
1 5

<210> SEQ ID NO 25
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: S is S or T
<220> FEATURE:
<221> NAME/KEY: MISC_FEATURE
<222> LOCATION: (1)..(6)
<223> OTHER INFORMATION: S is S or T
Xaa can be any naturally occurring amino acid

<400> SEQUENCE: 25

Ser Pro Asp Xaa Pro His
1 5

<210> SEQ ID NO 26
<211> LENGTH: 5
<212> TYPE: PRT
<213> ORGANISM: Artificial Sequence
<220> FEATURE:
<223> OTHER INFORMATION: synthetic construct

<400> SEQUENCE: 26

-continued

```
Asp Ser Pro His Asp
1               5


<210> SEQ ID NO 27
<211> LENGTH: 12
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(12)
<223> OTHER INFORMATION: Xaa can be any naturally occurring amino acid

<400> SEQUENCE: 27

Xaa Xaa Xaa Xaa Xaa Xaa Xaa Xaa Xaa Xaa Xaa Xaa
1               5                   10


<210> SEQ ID NO 28
<211> LENGTH: 4
<212> TYPE: PRT
<213> ORGANISM: Artificial Sequence
<220> FEATURE:
<223> OTHER INFORMATION: synthetic construct

<400> SEQUENCE: 28

Gly Gly Gly Ser
1


<210> SEQ ID NO 29
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: Xaa can be any naturally occurring amino acid

<400> SEQUENCE: 29

Tyr Xaa Xaa Thr Leu Xaa Tyr
1               5


<210> SEQ ID NO 30
<211> LENGTH: 17
<212> TYPE: PRT
<213> ORGANISM: Artificial Sequence
<220> FEATURE:
<223> OTHER INFORMATION: synthetic construct

<400> SEQUENCE: 30

Ala Pro Gln Pro Gly Leu Ala Ser Pro Asp Ser Pro His Asp Pro Cys
1               5                   10                  15

Lys


<210> SEQ ID NO 31
<211> LENGTH: 4
<212> TYPE: PRT
<213> ORGANISM: Artificial Sequence
<220> FEATURE:
<223> OTHER INFORMATION: synthetic construct

<400> SEQUENCE: 31

Asn Pro Val Glu
1
```

-continued

<210> SEQ ID NO 32
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: Y is Y or F
<220> FEATURE:
<221> NAME/KEY: MISC_FEATURE
<222> LOCATION: (1)..(7)
<223> OTHER INFORMATION: Y is Y or F
Xaa can be any naturally occurring amino acid
<220> FEATURE:
<221> NAME/KEY: MISC_FEATURE
<222> LOCATION: (8)..(8)
<223> OTHER INFORMATION: Y is Y or W

<400> SEQUENCE: 32

Tyr Xaa Xaa Thr Leu Xaa Tyr
1               5

<210> SEQ ID NO 33
<211> LENGTH: 4
<212> TYPE: PRT
<213> ORGANISM: Artificial Sequence
<220> FEATURE:
<223> OTHER INFORMATION: synthetic construct

<400> SEQUENCE: 33

His Cys Met Val
1

<210> SEQ ID NO 34
<211> LENGTH: 5
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (5)..(5)
<223> OTHER INFORMATION: M is M or L

<400> SEQUENCE: 34

Gly Ile Glu Asp Met
1               5

<210> SEQ ID NO 35
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (3)..(3)
<223> OTHER INFORMATION: V is V or I

<400> SEQUENCE: 35

Lys Pro Val Glu
1

<210> SEQ ID NO 36
<211> LENGTH: 5
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(5)
<223> OTHER INFORMATION: L is L or I
Xaa can be any naturally occurring amino acid
<220> FEATURE:
<221> NAME/KEY: MISC_FEATURE
<222> LOCATION: (2)..(2)
<223> OTHER INFORMATION: L is L or I

<400> SEQUENCE: 36

Pro Leu Xaa Asn Ala
1 5

<210> SEQ ID NO 37
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (3)..(3)
<223> OTHER INFORMATION: T is T or M or L

<400> SEQUENCE: 37

Thr Asn Thr Ser
1

<210> SEQ ID NO 38
<211> LENGTH: 12
<212> TYPE: PRT
<213> ORGANISM: Artificial Sequence
<220> FEATURE:
<223> OTHER INFORMATION: synthetic construct

<400> SEQUENCE: 38

His Ala Tyr Glu Ala Phe Arg Glu Lys Leu Ser Val
1 5 10

<210> SEQ ID NO 39
<211> LENGTH: 7
<212> TYPE: PRT
<213> ORGANISM: Artificial Sequence
<220> FEATURE:
<223> OTHER INFORMATION: misc_features
<220> FEATURE:
<221> NAME/KEY: MISC_FEATURE
<222> LOCATION: (1)..(7)
<223> OTHER INFORMATION: Xaa can be any naturally occurring amino acid

<400> SEQUENCE: 39

Tyr Xaa Pro Phe Thr Xaa Lys
1 5

<210> SEQ ID NO 40
<211> LENGTH: 12
<212> TYPE: PRT
<213> ORGANISM: Artificial Sequence
<220> FEATURE:
<223> OTHER INFORMATION: synthetic construct

<400> SEQUENCE: 40

Glu Leu Glu Lys Ala Tyr Lys Thr Thr Leu Ser Tyr
1 5 10

<210> SEQ ID NO 41
<211> LENGTH: 12
<212> TYPE: PRT

-continued

```
<213> ORGANISM: Artificial Sequence
<220> FEATURE:
<223> OTHER INFORMATION: synthetic construct

<400> SEQUENCE: 41

Asn Pro Val Glu Arg His Leu Trp His Pro Leu Met
1               5                   10


<210> SEQ ID NO 42
<211> LENGTH: 12
<212> TYPE: PRT
<213> ORGANISM: Artificial Sequence
<220> FEATURE:
<223> OTHER INFORMATION: synthetic construct

<400> SEQUENCE: 42

Ser Asn Val Leu Pro Trp Ser Pro Phe Gly Ser Thr
1               5                   10


<210> SEQ ID NO 43
<211> LENGTH: 5
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(1)
<223> OTHER INFORMATION: H is H or Y
<220> FEATURE:
<221> NAME/KEY: MISC_FEATURE
<222> LOCATION: (1)..(5)
<223> OTHER INFORMATION: H is H or Y
      Xaa can be any naturally occurring amino acid
<220> FEATURE:
<221> NAME/KEY: MISC_FEATURE
<222> LOCATION: (2)..(2)
<223> OTHER INFORMATION: Y is Y or W
<220> FEATURE:
<221> NAME/KEY: MISC_FEATURE
<222> LOCATION: (3)..(3)
<223> OTHER INFORMATION: H is H or R

<400> SEQUENCE: 43

His Tyr His Xaa Asn
1               5


<210> SEQ ID NO 44
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: P is P or A
      Xaa can be any naturally occurring amino acid
<220> FEATURE:
<221> NAME/KEY: MISC_FEATURE
<222> LOCATION: (3)..(3)
<223> OTHER INFORMATION: P is P or A

<400> SEQUENCE: 44

Tyr Xaa Pro Phe Thr Xaa Lys
1               5
```